(12) United States Patent
Dong et al.

(10) Patent No.: US 10,487,054 B2
(45) Date of Patent: Nov. 26, 2019

(54) THERAPEUTIC COMPOUNDS

(71) Applicant: REGENTS OF THE UNIVERSITY OF MINNESOTA, Minneapolis, MN (US)

(72) Inventors: Zigang Dong, Minneapolis, MN (US); Ann M. Bode, Minneapolis, MN (US); Kanamata Reddy, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 15/958,864

(22) Filed: Apr. 20, 2018

(65) Prior Publication Data
US 2018/0339966 A1    Nov. 29, 2018

Related U.S. Application Data

(60) Provisional application No. 62/488,566, filed on Apr. 21, 2017.

(51) Int. Cl.
| | | |
|---|---|---|
| *A61K 31/404* | (2006.01) | |
| *C07D 209/40* | (2006.01) | |
| *A61P 17/14* | (2006.01) | |
| *A61P 35/00* | (2006.01) | |

(52) U.S. Cl.
CPC ............ *C07D 209/40* (2013.01); *A61P 17/14* (2018.01); *A61P 35/00* (2018.01)

(58) Field of Classification Search
CPC .......................... C07D 209/40; A61K 31/404
See application file for complete search history.

(56) References Cited

U.S. PATENT DOCUMENTS

| | | | |
|---|---|---|---|
| 6,133,305 | A | 10/2000 | Tang et al. |
| 7,897,602 | B2 | 3/2011 | Huang et al. |
| 9,296,730 | B2 | 3/2016 | Bode et al. |
| 9,796,671 | B2 | 10/2017 | Bode et al. |
| 2004/0102509 | A1 | 5/2004 | Andrews et al. |
| 2010/0087464 | A1 | 4/2010 | Mi et al. |

FOREIGN PATENT DOCUMENTS

| | | | |
|---|---|---|---|
| JP | 2003064039 | * | 3/2003 |
| WO | 1995001349 | | 1/1995 |
| WO | 2000008202 | | 2/2000 |
| WO | 2006052936 | | 5/2006 |
| WO | 2011096676 | | 8/2011 |

OTHER PUBLICATIONS

Machine translation of JP2003064039, p. 1-11. (Year: 2003).*
Andrews, "Aurora kinases: shining lights on the therapeutic horizon?", Oncogene 24(32), 5005-5015 (2005).
Ayllon, et al., "PBK/TOPK promotes tumour cell proliferation through p38 MAPK activity and regulation of the DNA damage response", Oncogene 26, 3451-3461 (2007).
Barr, et al., "Aurora-A: the maker and breaker of spindle poles", J Cell Sci, 120(Pt 17), 2987-2996 (2007).
Beccalli, "Synthesis of the Carbazole Alkaloids Hyellazole and 6-Chlorohyellazole and Related Derivatives", J. Chem. Soc. Perkin Trans. 1, 579-587 (1994).
Bode, et al., "Mitogen-activated protein kinase activation in UV-induced signal transduction", Sci STKE 2003(167), Re2 (2003).
Burns, et al., "Extended UVB Exposures Alter Tumorigenesis and Treatment Efficacy in a Murine Model of Cutaneous Squamous Cell Carcinoma", J Skin Cancer 2013, 246848 (2013).
CAPLUS, Acession No. 2007-705774 (Jun. 28, 2007).
Carmena, et al., "The cellular geography of aurora kinases", Nat Rev Mol Cell Biol, 4(11), 842-854 (2003).
Carvajal, et al., "Aurora kinases: new targets for cancer therapy", Clin Cancer Res 12(23), 6869-6875 (2006).
Chen, et al., "Overexpression of an Aurora-C kinase-deficient mutant disrupts the Aurora-B/INCENP complex and induces polyploidy", J Biomed Sci 12(2), 297-310 (2005).
Chiang, et al., "Discovery of Pyrrole-Indolin-2-ones as Aurora Kinase Inhibitors with a Different Inhibition Profile", J. Med. Chem., 53(16), 5929-5941 (2010).
Chouhan, et al., "Regiospecific Epoxide Opening: A Facile Approach for the Synthesis of 3-Hydroxy-3-Aminomethylindolin-2-one Derivatives", Green Chemistry 13, 2553-2560 (2011).
Cooper, et al., "Ultraviolet B Regulation of Transcription Factor Families: Roles of Nuclear Factor-kappa B (NF-κB) and Activator Protein-1 (AP-1) in UVB-Induced Skin Carcinogenesis", Curr Cancer Drug Targets 7, 325-334 (2007).
De Gruijl, "Photocarcinogenesis: UVA vs UVB", Methods Enzymol 319, 359-366 (2000).
De Gruijl, et al., "UV-induced DNA damage, repair, mutations and oncogenic pathways in skin cancer", J Photochem Photobiol B 63, 19-27 (2001).

(Continued)

*Primary Examiner* — Karen Cheng
(74) *Attorney, Agent, or Firm* — Viksnins Harris Padys Malen LLP

(57) ABSTRACT

The invention provides a compound of formula I:

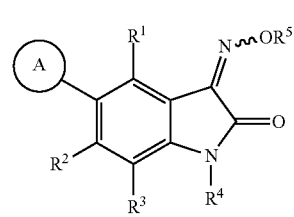

or a salt thereof, wherein $R^1$, $R^2$, $R^3$, $R^4$ and ring A have any of the values described in the specification, as well as compositions comprising a compound of formula I. The compounds are useful as anti-cancer agents.

15 Claims, 20 Drawing Sheets
Specification includes a Sequence Listing.

(56) References Cited

OTHER PUBLICATIONS

Ditchfield, et al., "Aurora B couples chromosome alignment with anaphase by targeting BubR1, Mad2, and Cenp-E to kinetochores", J Cell Biol 161(2), 267-280 (2003).
Elinson, et al., "Electrochemically Induced Henry Reaction of Nitromethane and Carbonyl Compounds", Tetrahedron 64, 5915-5919 (2008).
Gao, et al., "ADA-07 Suppresses Solar Ultraviolet-Induced Skin Carcinogenesis by Directly Inhibiting TOPK", Mol Cancer Ther 16(9), 1843-1854 (2017).
Gorgun, et al., "A novel Aurora-A kinase inhibitor MLN8237 induces cytotoxicity and cell-cycle arrest in multiple myeloma", Blood 115(25), 5202-5213 (2010).
Harrington, et al., "VX-680, a potent and selective small-molecule inhibitor of the Aurora kinases, suppresses tumor growth in vivo", Nat Med 10(3), 262-267 (2004).
Hauf, et al., "The small molecule Hesperadin reveals a role for Aurora B in correcting kinetochore-microtubule attachment and in maintaining the spindle assembly chechpoint", J Cell Biol 161(2) 281-294 (2003).
Hu, et al., "PBK/TOPK interacts with the DBD domain of tumor suppressor p53 and modulates expression of transcriptional targets including p21", Oncogene 29, 564-5474 (2010).
Jackson, et al., "Targeted anti-mitotic therapies: can we improve on tubulin agents?", Nat Rev Cancer, 7(2), 107-117 (2007).
Jung, et al., "Myricetin Suppresses UVB-Induced Skin Cancer by Targeting Fyn", Cancer Res 68, 6021-6029 (2008).
Kallio, et al., "Inhibition of aurora B kinase blocks chromosome segregation, overrides the spindle checkpoint, and perturbs microtubule dynamics in mitosis", Curr Biol 12(11), 900-905 (2002).
Kazimierczuk, et al., "Studies on the Adamantylation of N-Heterocycles and Nucleosides", Helvetica 82(11), 2020-2027 (1999).
Keppel Hesselilnk, "NS1209/SPD 502, A Novel Selective AMPA Antagonist for Stroke, Neuropathic Pain or Epilepsy? Drug Development Lessons Learned", Drug Dev Res 78(2), 75-80 (2017).
Kim, et al., "Novel TOPK Inhibitor HI-TOPK-032 Effectively Suppresses Colon Cancer Growth", Cancer Res 72, 3060-3068 (2012).
Kollareddy, et al., "Aurora kinase inhibitors: Progress towards the clinic", Invest New Drugs 30(6), 2411-2432 (2012).
Li, et al., "Asymmetric Nitroaldol Reactions of Nitroalkanes with Isatins Catalyzed by Bifunctional Cinchona Alkaloid Derivatives", European Journal of Organic Chemistry, vol. 2011 (27), 5237-5241 (2011).
Liu, et al. "Asymmetric cross aldol addition of isatins with alpha, beta-unsaturated ketones catalyzed by a bifunctional Bronsted acid-Bronsted base organcatalyst", Tetrahedron 68, 3843-3850 (2012).
Liu, et al. "Catalytic Enantioselective Henry Reactions of Isatines: Application in the Concise Synthesis fo (s)-(-)-Spirobrassinin", Chemistry 17(28), 7791-7795 (2011).
Lopez-Camarillo, et al., "Protein Kinases and Transcription Factors Activation in Response to UV-Radiation of Skin: Implications for Carcinogenesis", Int J Mol Sci 13, 142-172 (2012).
Marks, "An overview of skin cancers. Incidence and causation", Cancer 75, 607-612 (1995).
Marumoto, et al., "Aurora-A—a guardian of poles", Nat Rev Cancer 5(1), 42-50 (2005).
Matsuo, et al., "TOPK inhibitor induces complete tumor regression in xenograft models of human cancer through inhibition of cytokinesis", Sci Transl Med 6, 259ra145 (2014).
Meshram, et al., "An Efficient and Environmentally Friendly DABCO Catalyzed Henry Reaction of Isatins", Tetrahedron Letters 52, 5862-5864 (2011).
Prakash, et al., "Indolin-2-Ones in Clinical Trials as Potential Kinase Inhibitors: A Review", Pharmacology & Pharmacy, 3, 62-71 (2012).
Rogers, et al., "Incidence Estimate of Nonmelanoma Skin Cancer (Keratinocyte Carcinomas) in the U.S. Population, 2012", JAMA Dermatol 151, 1081-1086 (2015).
Samarasinghe, "Management of high-risk squamous cell carcinoma of the skin", Expert Rev Anticancer Ther 11, 763-769 (2011).
Sarasin, "The molecular pathways of ultraviolet-induced carcinogenesis", Mutat Res 428, 5-10 (1999).
Stern, "Prevalence of a history of skin cancer in 2007: results of an incidence-based model", Arch Dermatol 146, 279-282 (2010).
Xie, et al., "Discovery of the Novel mTOR Inhibitor and its Antitumor Activities In Vitro and In Vivo", Mol Cancer Ther 12(6), 950-958 (2013).
Xie, et al., "Identification of (E)-3-((E)-4-(benzo[d][1,3]dioxol-5-yl)-2-oxobut-3-en-1-ylidene)indolin-2-one as a novel Aurora B inhibitor both in vitro and in vivo", Cancer Res 73(2), 716-724 (2013).
Yang, et al., "AZD1152, a novel and selective aurora B kinase inhibitor, induces growth arrest, apoptosis, and sensitization for tubulin depolymerizing agent or topoisomerase II inhibitor in human acute leukemia cells in vitro and in vivo", Blood 110(6), 2034-2040 (2007).
Zhu et al., "Bidirectional signals transduced by TOPK-ERK interaction increase tumorigenesis of HCT116 colorectal cancer cells", Gastroenterology 133, 219-231 (2007).
Zykova, et al., "T-LAK Cell-originated Protein Kinase (TOPK) Phosphorylation of Prx1 at Ser-32 Prevents UVB-Induced Apoptosis in RPMI7951 Melanoma Cells through the Regulation of Prx1 Peroxidase Activity", J Biol Chem 285, 29138-29146 (2010).

* cited by examiner

Figure 5E
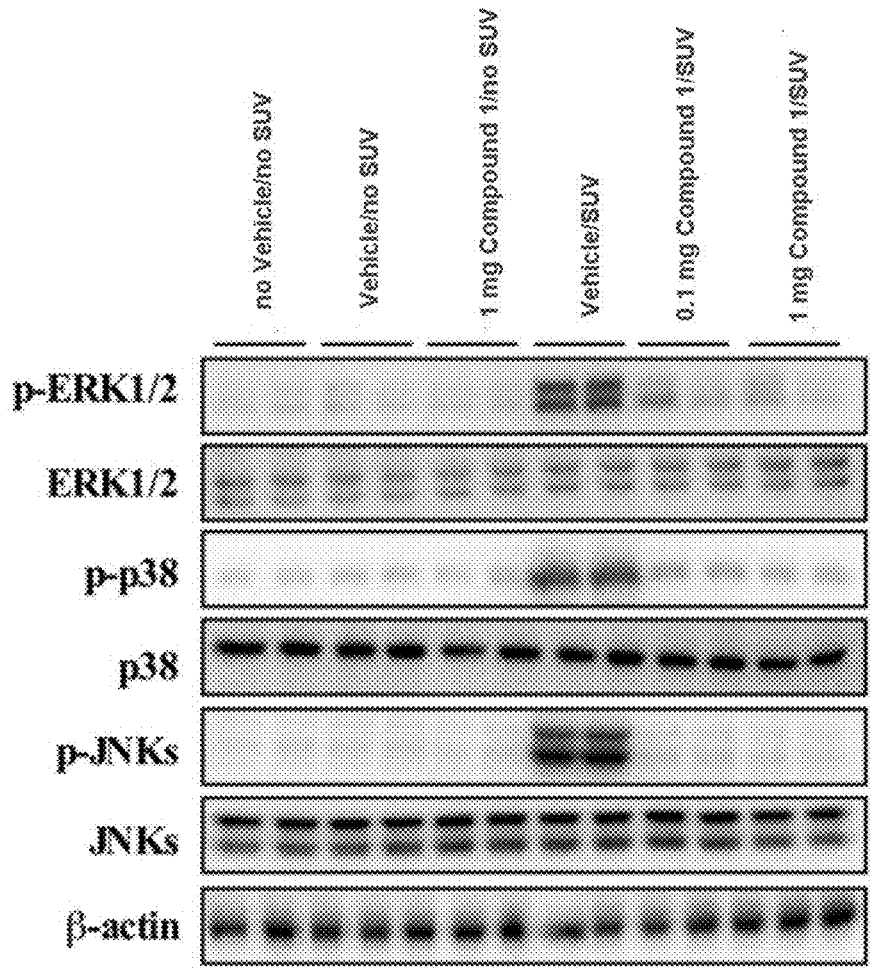
Figure 6A
Figure 6B
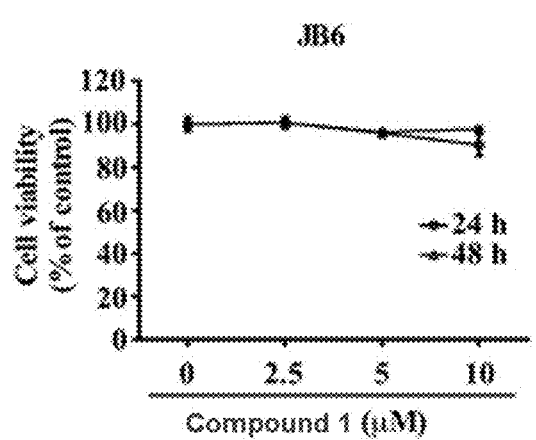
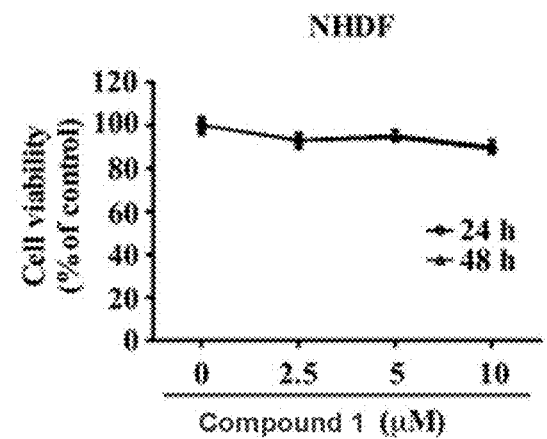

SEQUENCE LISTING

<160> NUMBER OF SEQ ID NOS: 2

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ccgggaatat ggcaagaggg ttaaactcga gtttaaccct cttgccatat tcttttt    57

<210> SEQ ID NO 2
<211> LENGTH: 57

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccggcaccaa gcaaattatc agaaactcga gtttctgata atttgcttgg tgttttt        57
```

THERAPEUTIC COMPOUNDS

PRIORITY

This application claims priority to U.S. Provisional Patent Application No. 62/488,566, filed 21 Apr. 2017. The entire content of this United States Provisional Patent Application is hereby incorporated herein by reference.

GOVERNMENT FUNDING

This invention was made with government support under CA027502, CA166011, CA187027 and CA196639 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Aug. 10, 2018, is named 09531_438US1_SL.txt and is 741 bytes in size.

BACKGROUND

Skin cancer is one of the most frequently diagnosed malignancies in the United States, and its incidence has been increasing at an astonishing rate over the past few decades, exceeding the number of all other human cancers combined (Stern, R. S., Arch Dermatol, 2010. 146: p. 279-82). Non-melanoma skin cancer (NMSC) includes basal cell carcinomas (BCC) and squamous cell carcinomas (SCC) and is the most common type of skin cancer with substantial associated morbidity and mortality (Rogers, H. W., et al., JAMA Dermatol, 2015. 151: p. 1081-6). BCCs comprise approximately 80% of skin cancers with SCC as the second most common skin cancer. SCCs are more aggressive and have a higher potential for metastasis compared to BCCs (Samarasinghe, V., et al., Expert Rev Anticancer Ther, 2011. 11: p. 763-9). Solar ultraviolet (SUV) irradiation is well documented as a prominent environmental carcinogen responsible for various physiological and biological effects, including immune suppression, cellular aging, and DNA damage (de Gruijl, F. R., et al., J Photochem Photobiol B, 2001. 63: p. 19-27; and Lopez-Camarillo, C., et al., Int J Mol Sci, 2012. 13: p. 142-72). Furthermore, strong epidemiological and molecular evidence indicates that cumulative exposure to SUV irradiation is the major etiologic factor in the development of NMSC (Burns, E. M., et al., J Skin Cancer, 2013. 2013: p. 246848; Marks, R., Cancer, 1995. 75: p. 607-12; and Sarasin, A., Mutat Res, 1999. 428: p. 5-10). The SUV spectrum can be divided into 3 subtypes according to wavelength and include UVA (320-400 nm), UVB (280-320 nm) and UVC (200-280 nm) (Jung, S. K., et al., Cancer Res, 2008. 68: p. 6021-9). Previous studies indicated that although UVC is filtered out by stratospheric ozone, UVA and UVB each has strong carcinogenic effects on the skin, which can lead to DNA damage, erythema, sunburn, immunosuppression, and, eventually, skin cancer (Lopez-Camarillo, C., et al., Int J Mol Sci, 2012. 13: p. 142-72; Cooper, S. J., et al., Curr Cancer Drug Targets, 2007. 7: p. 325-34; and de Gruijl, F. R., Methods Enzymol, 2000. 319: p. 359-66). Therefore, targeting SUV-induced signaling could be an effective strategy for developing agents for effective chemoprevention and chemotherapy against skin carcinogenesis.

Activation of intracellular signaling pathways in response to SUV irradiation plays a crucial role in SUV-induced skin cancer. The mitogen-activated protein kinases (MAPKs) are serine/threonine protein kinases that are strongly activated by SUV irradiation, and are essential in the regulation of fundamental cellular processes, such as proliferation, differentiation, and apoptosis (Bode, A. M., et al., Sci STKE, 2003. 2003: p. Re2). The MAPK cascades comprise the extracellular signal-regulated kinases (ERKs), p38 MAPKs, and c-Jun $NH_2$-terminal kinases (JNKs). The activation of these pathways occurs rapidly and is vital in the regulation of SUV-induced cellular responses that can lead to skin carcinogenesis (Bode, A. M., et al., Sci STKE, 2003. 2003: p. Re2). T-LAK cell-originated protein kinase (TOPK) is a member of the MEK3/6-related MAPKK family and is highly expressed in many cancers (Zhu, F., et al., Gastroenterology, 2007. 133: p. 219-31). TOPK is an upstream activator of ERKs, p38 MAPKs and JNKs and has been identified as an oncogenic protein that is involved in various cellular functions, such as DNA damage, neoplastic transformation and inflammation (Ayllon, V., et al., Oncogene, 2007. 26: p. 3451-61; Hu, F., et al., Oncogene, 2010. 29: p. 5464-74; and Zykova, T. A., et al., J Biol Chem, 2010. 285: p. 29138-46). Moreover, an accumulation of data provides evidence that the inhibition of TOPK might be useful in cancer chemoprevention and treatment (Kim, D. J., et al., Cancer Res, 2012. 72: p. 3060-8; and Matsuo, Y., et al., Sci Transl Med, 2014. 6: p. 259ra145). However, very few effective TOPK inhibitors have been discovered. Currently, there is a need for agents that are useful for treating cancer. Specifically, there is a need for compounds that inhibit the activity of TOPK.

SUMMARY

In one aspect the present invention provides compounds inhibiting the activity of TOPK that are useful for treating cancer. Accordingly, the invention provides a compound of formula I:

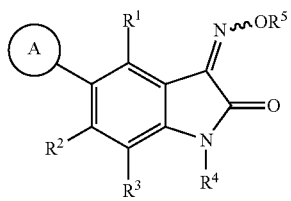

wherein:
ring A is a 3-15 membered cycloalkyl that is optionally substituted with one or more groups selected from halo, hydroxy, nitro, cyano, $NR^aR^b$, $C_{1-6}$ alkyl, $C_{1-6}$ alkoxy, or $C_{1-6}$ haloalkyl, $R^1$ is hydrogen, halo, hydroxy, nitro, cyano, $NR^cR^d$, $C_{1-6}$ alkyl, $C_{1-6}$ alkoxy, or $C_{1-6}$ haloalkyl;

$R^2$ is hydrogen, halo, hydroxy, nitro, cyano, $NR^eR^f$, $C_{1-6}$ alkyl, $C_{1-6}$ alkoxy, or $C_{1-6}$ haloalkyl;

$R^3$ is hydrogen, halo, hydroxy, nitro, cyano, $NR^gR^h$, $C_{1-6}$ alkyl, $C_{1-6}$ alkoxy, or $C_{1-6}$ haloalkyl;

$R^4$ is hydrogen, $C_{1-6}$ alkyl, or $C_{1-6}$ haloalkyl;

$R^5$ is hydrogen, $C_{1-6}$ alkyl, aryl, or heteroaryl, wherein the $C_{1-6}$ alkyl is optionally substituted with one or more groups selected from halo, aryl, heteroaryl, hydroxy, $C_{1-6}$ alkoxy, carboxy, or $NR^iR^j$;

each of $R^a$ and $R^b$ is independently selected from H and $C_{1-6}$ alkyl, or $R^a$ and $R^b$ together with the nitrogen to which they are attached form aziridino, azetidino, morpholino, piperazino, pyrrolidino or piperidino;

each of $R^c$ and $R^d$ is independently selected from H and $C_{1-6}$ alkyl, or $R^c$ and $R^d$ together with the nitrogen to which they are attached form aziridino, azetidino, morpholino, piperazino, pyrrolidino or piperidino;

each of $R^e$ and $R^f$ is independently selected from H and $C_{1-6}$ alkyl, or $R^e$ and $R^f$ together with the nitrogen to which they are attached form aziridino, azetidino, morpholino, piperazino, pyrrolidino or piperidino; and each of $R^g$ and $R^h$ is independently selected from H and $C_{1-6}$ alkyl, or $R^g$ and $R^h$ together with the nitrogen to which they are attached form aziridino, azetidino, morpholino, piperazino, pyrrolidino or piperidino; and each of $R^i$ and $R^j$ is independently selected from H and $C_{1-6}$ alkyl, or $R^i$ and $R^j$ together with the nitrogen to which they are attached form aziridino, azetidino, morpholino, piperazino, pyrrolidino or piperidino;

or a salt thereof.

The invention also provides a pharmaceutical composition comprising a compound of formula I or a pharmaceutically acceptable salt thereof, and a pharmaceutically acceptable excipient.

The invention also provides a method for treating or preventing cancer in an animal (e.g., a mammal such as a human) comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of cancer.

The invention also provides the use of a compound of formula I or a pharmaceutically acceptable salt thereof to prepare a medicament for treating cancer in an animal (e.g. a mammal such as a human).

The invention also provides a compound of formula I as described in any one of claims 1-9, or a pharmaceutically acceptable salt thereof, for use in prophylactic or therapeutic treatment of hair loss.

The invention also provides the use of a compound of formula I as described in any one of claims 1-9, or a pharmaceutically acceptable salt thereof, for the manufacture of a medicament for the treatment of hair loss in an animal.

The invention also provides a compound of formula I as described in any one of claims 1-9, or a pharmaceutically acceptable salt thereof, for use in prophylactic or therapeutic treatment of a disease associated with the activity of T-LAK cell-originated protein kinase (TOPK).

The invention also provides the use of a compound of formula I as described in any one of claims 1-9, or a pharmaceutically acceptable salt thereof, for the manufacture of a medicament for the treatment of a disease associated with the activity of T-LAK cell-originated protein kinase (TOPK) in an animal.

The invention also provides processes and intermediates disclosed herein that are useful for preparing a compound of formula I or a salt thereof.

BRIEF DESCRIPTION OF THE FIGURES

FIG. 5E shows compound 1 inhibits SUV-induced phosphorylation of ERK1/2, p38, and JNKs in mouse skin. The expression levels of phosphorylated and total proteins were analyzed by Western blot.

FIG. 6A shows compound 1 has no cytotoxicity against the JB6 P+ mouse epidermal skin cell line. FIG. 6B shows compound 1 has no cytotoxicity against normal human dermal fibroblasts (NHDF). Cells (1×10$^4$ cells/well) were seeded into 96-well plates. After an overnight incubation, cells were treated with different concentrations of compound 1 and incubated for 24 or 48 h. Then 20 μL of the CellTiter 96 Aqueous One Solution (Promega, Madison, Wis.) were added to each well and cells were incubated for an additional 1 h at 37° C. Absorbance was measured at an optical density of 492 and 690 nm using the Thermo Multiskan plate-reader (Thermo Fisher Scientific, Waltham, Mass.).

DETAILED DESCRIPTION

Figure 1A:
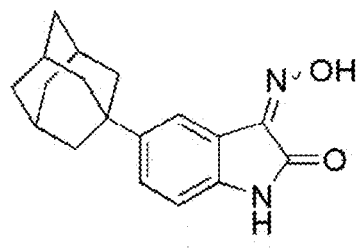
FIG. 1A shows chemical structure of compound 1.

The following definitions are used, unless otherwise described: halo or halogen is fluoro, chloro, bromo, or iodo.

Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-6}$ means one to six carbons). Examples include $(C_1-C_6)$alkyl, $(C_2-C_6)$alkyl and $(C_3-C_6)$ alkyl. Examples of alkyl groups include methyl, ethyl, n-propyl, iso-propyl, n-butyl, t-butyl, iso-butyl, sec-butyl, n-pentyl, and n-hexyl.

The term "haloalkyl" refers to an alkyl substituted with one or more halo groups (e.g., $(C_1-C_6)$haloalkyl. Non limiting examples of "haloalkyl" include iodomethyl, bromomethyl, chloromethyl, fluoromethyl, trifluoromethyl, 2-chloroethyl, 2-fluoroethyl, 2,2,2-trifluoroethyl 2,2-difluoroethyl and pentafluoroethyl.

The term "alkoxy" refers to an alkyl groups attached to the remainder of the molecule via an oxygen atom ("oxy"). Non limiting examples of "alkoxy" include methoxy, ethoxy, propoxy, isopropoxy, butoxy, iso-butoxy, sec-butoxy, pentoxy, 3-pentoxy, or hexyloxy.

The term "cycloalkyl" refers to a saturated or partially unsaturated all carbon ring having 3 to 8 carbon atoms (i.e., $(C_3-C_8)$carbocycle). The term also includes multiple condensed, saturated all carbon ring systems (e.g., ring systems comprising 2, 3 or 4 carbocyclic rings).

Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2] octane, etc). Non-limiting examples of cycloalkyls include cyclopropyl, cyclobutyl, cyclopentyl, cyclohexyl, bicyclo [2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., cycloalkyl. Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, and heteroaryl It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The compounds disclosed herein can also exist as tautomeric isomers in certain cases. Although only one delocalized resonance structure may be depicted, all such forms are contemplated within the scope of the invention. In one embodiment, the compound of formula Ia exists as a mixture of the following tautomeric isomers:

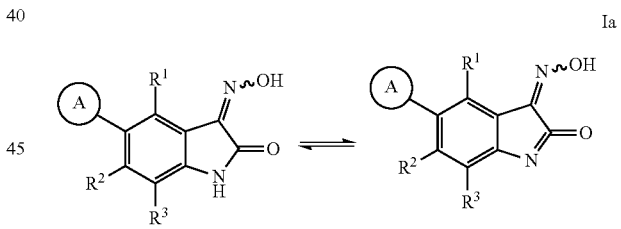

Ia

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

In one embodiment, A is a 6-12 membered cycloalkyl that is optionally substituted with one or more groups selected from halo, hydroxy, nitro, cyano, $NR^aR^b$, $C_{1-6}$ alkyl, $C_{1-6}$ alkoxy, or $C_{1-6}$ haloalkyl.

In one embodiment, A is a 8-11 membered cycloalkyl that is optionally substituted with one or more groups selected from halo, hydroxy, nitro, cyano, $NR^aR^b$, $C_{1-6}$ alkyl, $C_{1-6}$ alkoxy, or $C_{1-6}$ haloalkyl.

In one embodiment, A is adamantyl.
In one embodiment, $R^1$ is hydrogen.
In one embodiment, $R^2$ is hydrogen.
In one embodiment, $R^3$ is hydrogen.
In one embodiment, $R^4$ is hydrogen.
In one embodiment, $R^5$ is hydrogen or $C_{1-6}$ alkyl.
In one embodiment, $R^5$ is hydrogen.
In one embodiment, the compound of formula I is:

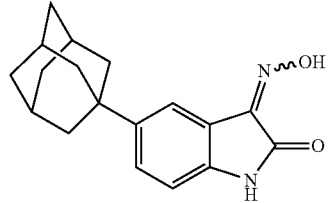 [SMILES: O=C1Nc2ccc(C34CC5CC(CC(C5)C3)C4)cc2C1=NO]

or a salt thereof.

In one embodiment, the cancer is selected from the group consisting of skin cancer, pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors.

In one embodiment, the cancer is skin cancer.
In one embodiment, the cancer is solar ultraviolet (SUV)-induced skin cancer.

In one aspect, the invention provides a method to treat hair loss in a mammal comprising administering a compound of formula I, or a pharmaceutically acceptable salt thereof, to the mammal.

In another aspect, the invention provides a method to inhibit the activity of T-LAK cell-originated protein kinase (TOPK) in vitro or in vivo comprising contacting the kinase with a compound of formula I, or a pharmaceutically acceptable salt thereof.

In one aspect, the invention provides a compound of formula I, or a pharmaceutically acceptable salt thereof, for use in prophylactic or therapeutic treatment of hair loss in a mammal.

In one aspect, the invention provides the use of a compound of formula I, or a pharmaceutically acceptable salt thereof, for the manufacture of a medicament for the treatment of hair loss in an animal.

In one aspect, the invention provides a compound of formula I, or a pharmaceutically acceptable salt thereof, for use in prophylactic or therapeutic treatment of a disease associated with the activity of T-LAK cell-originated protein kinase (TOPK).

In one aspect, the invention provides the use of a compound of formula I, or a pharmaceutically acceptable salt thereof, for the manufacture of a medicament for the treatment of a disease associated with the activity of T-LAK cell-originated protein kinase (TOPK) in an animal.

Processes for preparing compounds of formula I are provided as further embodiments of the invention and are illustrated by the following procedures in which the meanings of the generic radicals are as given above unless otherwise qualified.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S.

Pat. No. 4,608,392), Geria (U.S. Pat. No. 4,992,478), Smith et al. (U.S. Pat. No. 4,559,157) and Wortzman (U.S. Pat. No. 4,820,508).

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treating cancer. Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal to treat cancer Compounds of invention can be prepared using known methods or using procedures analogous to those described in the examples herein. For example, compounds of invention can be prepared as illustrated in the following scheme.

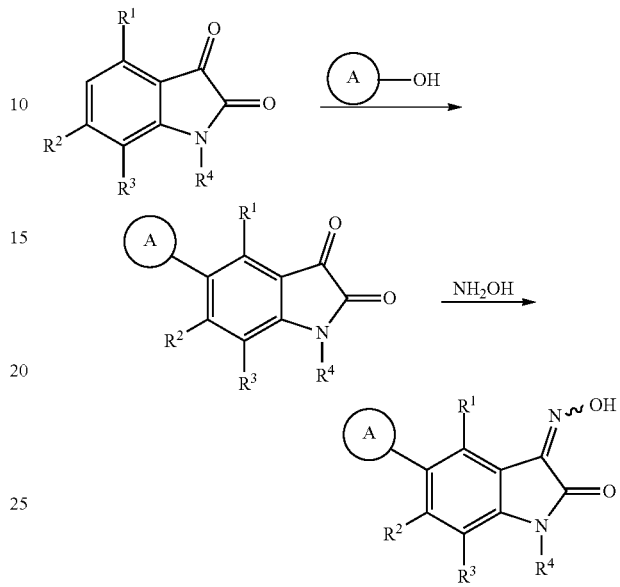

The invention will now be illustrated by the following non-limiting Examples.

EXAMPLES

Example 1. Synthesis of compound 5-(adamantan-1-yl)-3-(hydroxyimino)indolin-2-one (1)

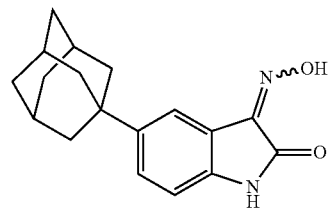 [SMILES: O=C1Nc2ccc(C34CC5CC(CC(C5)C3)C4)cc2C1=NO]

Step 1. Preparation of 5-(adamantan-1-yl)indoline-2,3-dione

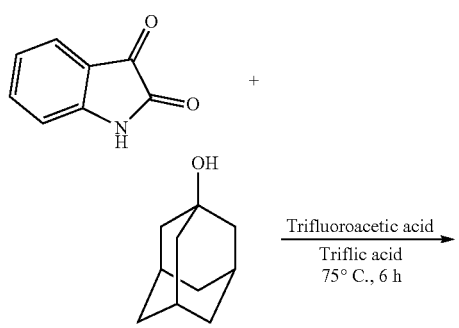

-continued

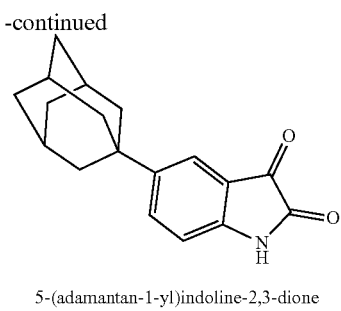

5-(adamantan-1-yl)indoline-2,3-dione

To a stirred solution of isatin (1.47 g, 10 mmol) and 1-adamantanol (1.52 g, 10 mmol) in trifluoroacetic acid (10 ml) was added triflic acid (1.95 g, 13 mmol). The resulting mixture was stirred at 75° C. for 6 h. After this time, the reaction mixture was cooled to r.t. and diluted with EtOH/H2O 2:8 (50 ml). The obtained red precipitate was filtered and purified by column chromatography (10% methanol in DCM).

Step 2. Preparation of 5-(adamantan-1-yl)-3-(hydroxyimino)indolin-2-one (1)

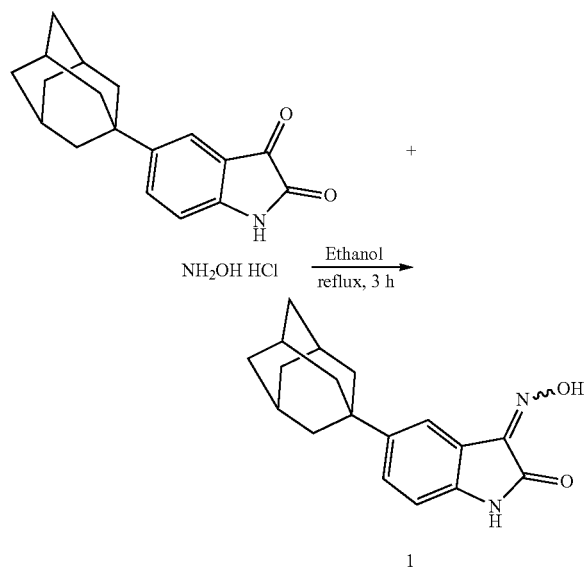

To the stirred solution of 5-(adamantan-1-yl)indoline-2,3-dione (2.0 g) in ethanol (20 ml), hydroxylamine hydrochloride (0.74 g, 1.5 eq) was added and the mixture was refluxed for about 3 h. After completion of the reaction, the solvent was evaporated and purified by column chromatography (5% Methanol in DCM).

Example 2. Biological Evaluation of Compound 1

Chemicals and Reagents

Cell culture media were all obtained from Invitrogen (Grand Island, N.Y.). Fetal bovine serum (FBS) was from Gemini Bio-Products (West Sacramento, Calif.). Tris, NaCl, and SDS for molecular biology and buffer preparation were purchased from Sigma-Aldrich (St. Louis, Mo.). The active TOPK and MEK1 human recombinant proteins for the kinase assays were from SignalChem (Richmond, BC, Canada) and Millipore (Billerica, Mass.), respectively. The antibodies against phosphorylated TOPK (Thr9), ERK1/2 (Thr202/204), p38, JNKs, c-Jun and total TOPK, ERK1/2, p38, JNKs, p-c-Jun and PCNA were from Cell Signaling Biotechnology (Danvers, Mass.). Antibodies to detect β-actin was purchased from Santa Cruz Biotechnology (Santa Cruz, Calif.). The CellTiter 96 Aqueous One Solution Cell Proliferation Assay Kit and the luciferase assay substrate were purchased from Promega (Madison, Wis.). CNBr-activated Sepharose™ 4B beads were purchased from GE Healthcare Bio-Sciences (Uppsala, Sweden).

Cell Culture

The human skin keratinocytes (HaCaT cells), normal human dermal fibroblasts (NHDF), JB6 P+ mouse epidermal cells, human epidermoid carcinoma A431 cells and the HEK293T cell line were purchased from American Type Culture Collection (ATCC; Manassas, Va.). The human squamous cell carcinoma SCC12 cell line was purchased from Thermo Fisher Scientific (Waltham, Mass.). All the cell lines were cytogenetically tested and authenticated before freezing. Each vial was thawed and maintained for a maximum of 10 passages. JB6 P+ mouse epidermal skin cells were cultured in Eagle's Minimum Essential Medium (MEM) with 5% FBS and 1% antibiotics. The HaCaT, NHDF, HEK293T and A431 cells were cultured in Dulbecco's modified Eagle's medium (DMEM) containing 10% FBS and 1% antibiotics. The SCC12 cell line was cultured in Dulbecco's modified Eagle's medium/Ham's F-12-50/50 Mix (DMEM: F-12K 50/50) medium supplemented with 10% FBS and 1% antibiotics. All cell culture conditions were performed following ATCC's instructions.

MTS Assay

Cells ($1\times10^4$ cells/well) were seeded into 96-well plates for determining cytotoxicity. After an overnight incubation, cells were treated with different concentrations of compound 1 and incubated for 24 or 48 h. Then 20 µL of the CellTiter 96 Aqueous One Solution (Promega Corporation, Madison, Wis.) were added to each well and cells were incubated for an additional 1 h at 37° C. Absorbance was measured at an optical density of 492 and 690 nm using the Thermo Multiskan plate-reader (Thermo Fisher Scientific, Waltham, Mass.).

Anchorage-Independent Cell Growth Assay

Cells ($8\times10^3$/well) were seeded into 6-well plates with 0.3% Basal Medium Eagle agar containing 10% FBS with epidermal growth factor (EGF, 10 ng/ml) and different concentrations of compound 1 and then cultured for 1 to 2 weeks. Colonies were scored under a microscope using the Image-Pro PLUS (v6.) computer software program (Media Cybernetics. Rockville, Md.).

Crystal Violet Staining Assay

Cell proliferation was determined by a crystal violet staining assay. Cells ($3\times10^4$/well) were seeded into 24-well plates. After an overnight incubation, cells were treated with different concentrations of compound 1 and incubated for several days. Then, each well was washed 3 times with phosphate buffered saline (PBS) and stained with 0.2% (w/v) crystal violet in 2% (v/v) ethanol. After 10 min, cells were washed 3 times with distilled water, and the remaining dye was dissolved in 0.5% (w/v) sodium dodecyl sulfate in 50% (v/v) ethanol. Absorbance was measured at an optical density of 540 nm using the Thermo Multiskan plate-reader (Thermo Fisher Scientific).

SUV Irradiation System

The SUV irradiation system (UVA-340 lamps) was purchased from Q-Lab Corporation (Cleveland, Ohio) and used to stimulate cells in this study. The UVA-340 lamps provide the best possible simulation of sunlight in the critical short wavelength region from 365 nm down to the solar cutoff of 295 nm with a peak emission of 340 nm (Nakano, H., et al., Photochem Photobiol, 2001. 74: p. 274-82). Using this system, cells were exposed once at a dose of 60 kJ UVA/m$^2$ and 2.9 kJ UVB/m$^2$.

Western Blot Analysis

HaCaT or JB6 P+ cells (1×10$^6$) were cultured in 10-cm dishes for 24 h and then the medium was replaced with 0.1% FBS medium for 24 h. Cells were then treated with different concentrations of compound 1 for 4 h followed by exposure to SUV (60 kJ UVA/m$^2$ and 2.9 kJ UVB/m$^2$). After SUV, cells were incubated for 15 min at 37° C. in a 5% CO$_2$ humidified incubator. SCC12 and A431 cells (1.5×10$^6$) were cultured in 10-cm dishes overnight and then starved for 24 h. Cells were then treated with different concentrations of compound 1 for an additional 24 h. Protein concentration in cell lysates was determined using a protein assay kit (Bio-Rad Laboratories, Hercules, Calif.). Equal amounts of proteins were resolved by SDS-PAGE and then transferred onto polyvinylidene difluoride (PVDF) membranes (EMD Millipore Corp., Billerica, Mass.) and membranes were blocked with 5% nonfat milk for 1 h at room temperature. Blots were probed with appropriate primary antibodies (1:1000) overnight at 4° C. followed by incubation with a horseradish peroxidase (HRP)-conjugated secondary antibody (1:5000) for hybridization. Protein bands were visualized with a chemiluminescent reagent (GE Healthcare Biosciences).

Lentiviral INFECTION

Lentivirus plasmids shTOPK (#1, TRCN0000001807; 5'-CCGGGAATATGGCAAGAGGGTTAAACTCGAGTT-TAACCCTCTTGCCATATTCTTTTT-3' (SEQ ID NO: 1), #2 TRCN0000001806; 5'-CCGGCACCAAGCAAAT-TATCAGAAACTCGAGTTTCTGA-TAATTTGCTTGGT-GTTTTT-3' (SEQ ID NO: 2)) were purchased from GE Healthcare Dharmacon (OpenBioSystem). pLKO.1-puro Non-Target shRNA Control Plasmid DNA was purchased from Sigma-Aldrich Co. LLC (St. Louis, Mo.). To generate knockdown TOPK cells, the lentiviral expression vector of TOPK or shRNA control plasmid DNA was transfected into HEK293T cells together with pMD2.0G and psPAX, which were purchased from Thermo Scientific (Huntsville, Ala.). Cells were transfected using iMFectin poly DNA transfection reagent (GenDEPOT) according to the manufacturer's instructions. Viral supernatant fractions were collected at 48 h after transfection and filtered through a 0.45 μm syringe filter followed by infection into the appropriate cells together with 10 μg/mL polybrene (Millipore). At 16 h after infection, the medium was replaced with fresh complete growth medium containing the appropriate concentration of puromycin. At 3 to 4 days after infection, the selected cells were used for experiments.

Luciferase Reporter Assay

Confluent monolayers of JB6 P+ cells stably transfected with an AP-1 luciferase reporter plasmid were trypsinized and viable cells (4×10$^4$) suspended in 1 ml of 5% FBS-MEM were added to each well of a 24-well plate. After a 24 h incubation at 37° C. in a 5% CO$_2$ humidified incubator, cells were starved in 0.1% serum medium for another 24 h and then treated with different concentrations of compound 1 for 1 h. Cells were then exposed to SUV (60 kJ UVA/m$^2$ and 2.9 kJ UVB/m$^2$) and harvested after a 3 h incubation. Finally, the cells were disrupted with 100 μl of lysis buffer (0.1 M potassium phosphate pH 7.8, 1% Triton X-100, 1 mM dithiothreitol (DTT), and 2 mM EDTA) and luciferase activity was measured using a luminometer (Luminoskan Ascent, Thermo Electro, Waltham, Mass.).

Stable control or TOPK knockdown cells were co-transfected with 100 ng of the AP-1 luciferase reporter plasmid and 50 ng of an internal control P3-galactosidase plasmid. Cells were transfected using iMFectin poly DNA transfection reagent (GenDEPOT) according to the manufacturer's instructions. After 12 h of transfection, cells were incubated with different concentrations of compound 1 for another 24 h. Luciferase and β-galactosidase activities were measured using the Luminoskan Ascent and Multiskan MCC (Labsystems), respectively. The luciferase activity was normalized to 3-galactosidase activity.

Pull-Down Assays

Compound 1 (2.5 mg) was coupled to CNBr-activated Sepharose 4B (GE Healthcare Biosciences, Pittsburgh, Pa.) matrix-beads (0.5 g) in 0.5 M NaCl and 40% DMSO (pH 8.3) overnight at 4° C., according to the manufacturer's instructions. Active TOPK, MEK or HaCaT cell lysates (500 μg) were mixed with compound 1-conjugated Sepharose 4B beads or with Sepharose 4B beads alone as a control in reaction buffer (50 mM Tris-HCl pH 7.5, 5 mM EDTA, 150 mM NaCl, 1 mM dithiothreitol [DTT], 0.01% NP-40, 2 μg/mL bovine serum albumin, 0.02 mM phenylmethylsulfonylfluoride [PMSF], and 1×protease inhibitor cocktail). After gentle rocking at 4° C. overnight, the beads were washed 5 times with buffer (50 mM Tris-HCl pH 7.5, 5 mM EDTA, 150 mM NaCl, 1 mM DTT, 0.01% NP-40, and 0.02 mM PMSF). Binding was examined by Western blotting. For the ATP competition assay, active TOPK (200 ng) was incubated with different concentrations of ATP (0, 10, or 100 μM) in reaction buffer at 4° C. overnight. compound 1-conjugated Sepharose 4B beads or Sepharose 4B beads alone were added and incubated at 4° C. overnight, followed by 5 washes with buffer. Then, binding was examined by Western blotting.

In Vitro Kinase Assay

The in vitro kinase assay was conducted according to the instructions provided by Millipore (Billerica, Mass.). Briefly, reactions were performed in the presence of 10 μCi [γ-$^{32}$P] ATP with active TOPK (200 ng) or MEK1 (200 ng), compound 1 (0.5, 1, 3, or 5 μM) or HI-032 (10 μM, in-house synthesis) or PD098059 (10 μM, Sigma) in 40 μL of reaction buffer (40 mM MOPS/NaOH pH 7.0, 1 mM EDTA, 10 mM MnCl$_2$, and 0.8 M ammonium sulphate) at 30° C. for 30 min. HI-032 or PD098059, a well-known TOPK or MEK1 inhibitor, was used as a positive control. Reactions were stopped by adding 10 μl protein loading buffer and the mixture was separated by SDS-PAGE. The relative amounts of incorporated radioactivity were assessed by autoradiography.

Molecular Modeling

The computer modeling of compound 1 with TOPK was performed using the Schrödinger Suite 2015 software programs (Schrödinger, Schrödinger Suite 2015. Schrödinger, LLC; New York, N.Y.: 2015). The TOPK crystal structures were prepared under the standard procedure of the Protein Preparation Wizard in Schrödinger Suite 2015. Hydrogen atoms were added consistent with a pH of 7 and all water molecules were removed. The ATP binding site-based receptor grid was generated for docking compound 1 was prepared using the LigPrep program (Schrödinger) and the lowest energy conformations for docking were determined by using default parameters under the extra precision (XP) mode and the program Glide. The protein-ligand docking analysis was conducted using the induced fit docking program of Schrödinger, which can provide the ligand binding flexibility with binding pocket residues.

Mouse Skin Tumorigenesis Study

Female SKH-1 hairless mice were purchased from Charles River and were acclimated for 2 weeks before the study and had free access to food and water. All animals were maintained according to the guidelines approved by the University of Minnesota Institutional Animal Care and Use Committee (IACUC). The animals were housed in climate-controlled quarters with a 12-h light/dark cycle. The skin carcinogenesis experiments were conducted using 6-8 wk old mice with a mean body weight of 25 g. Skin carcinogenesis was induced by a solar simulated ultraviolet irradiation system. The SUV irradiation source (Q-Lab Corporation, Westlake, Ohio) emitted at wavelengths of 295 to 365 nm and the peak emission was 340 nm.

The two mouse models included an early-stage prevention model and a late-stage prevention model. These models were designed for detecting either the respective chemopreventive effect or the potential therapeutic value of compound 1 against SUV-induced skin damage and carcinogenesis. For the early-stage prevention study, SKH-1 mice were divided into 7 groups and an oil-in-water emulsion cream was applied topically as the vehicle with or without compound 1. The three control groups included 1) mice (n=3) not treated with vehicle or SUV; 2) mice (n=3) treated with vehicle but no SUV; and 3) mice (n=3) treated with 1 mg compound 1 in vehicle but not exposed to SUV. Experimental groups included 1) mice (n=12) treated with SUV only; 2) mice (n=12) treated with vehicle followed by SUV 1 h later; 3) mice (n=12 each group) treated with topical application of 0.1 or 1 mg of compound 1 in vehicle 1 h before SUV irradiation. The topical applications and SUV treatment were applied 3 times a week for a total of 15 weeks. At 15 weeks, SUV irradiation was discontinued and topical applications continued with tumor growth monitoring for an additional 13 weeks until week 28 at which time mice were euthanized and tissues harvested.

For the late-stage prevention model, the control and experimental groups were identical to those for the early prevention model. However, the experimental groups of mice were exposed to SUV irradiation 3 times a week for 15 weeks without application of vehicle or compound 1 in vehicle. At the end of 15 weeks, SUV exposure was stopped and application of vehicle with or without compound 1 was begun and continued for 13 weeks until week 28 at which time the study was discontinued and mice euthanized and tissues harvested.

For both studies, the SUV irradiation was progressively increased by 10% each week. At week 1, mice were irradiated with SUV at a dose of 36 kJ/m$^2$ UVA and 1.8 kJ/m$^2$ UVB. At week 6, the dose of SUV reached 60 kJ/m$^2$ UVA and 2.9 kJ/m$^2$ UVB and this dose was maintained from week 6 to week 15. The respective doses of vehicle or compound 1 were applied topically to the dorsal area. Mice were weighed and tumors were measured once a week until week 28 or when tumor load reached 1 cm$^3$ total volume. At that time mice were euthanized and one-half of each sample was immediately fixed in 10% formalin and processed for hematoxylin and eosin (H&E) staining and immunohistochemistry. The other one-half of the sample was frozen and used for Western blot analysis.

Immunohistochemistry Staining

Skin tissues were embedded in paraffin and subjected to immunohistochemistry. Tissues were de-paraffinized and hydrated and then permeabilized with 0.5% Triton X-100/1×PBS for 10 min. Tissues were hybridized with PCNA (1:4000) as the primary antibody and biotinylated anti-mouse IgG as the secondary antibody. Slides were stained using the Vectastain Elite ABC Kit (Vector Laboratories, Inc., Burlingame, Calif.) to detect protein targets according to the manufacturer's instructions. After developing with 3, 3'-diaminobenzidine, the sections were counterstained with hematoxylin.

Statistical Analysis

All quantitative data are expressed as mean values±standard deviation (S.D.) of at least 3 independent experiments. Significant differences were determined by a Student t test or one-way ANOVA. A probability value of $p<0.05$ was used as the criterion for statistical significance.

Results

Compound 1 Inhibits Proliferation of NMSC Cells

Figure 7:
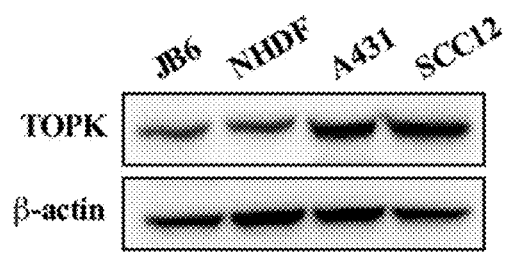
FIG. 7 shows the expression level of TOPK in normal skin cells (JB6 P+, NHDF) and skin cancer cells (A431 and SCC12). TOPK expression was assessed by Western blot using a specific antibody and β-actin was used as a loading control.

Because of the steady increase in skin cancer incidence, chemoprevention is a practical approach to the control of SUV-induced skin cancer that has received much public attention (Wright, T. I., et al., J Am Acad Dermatol, 2006. 54: p. 933-46). An accumulation of evidence has indicated that TOPK might be an attractive target for chemopreventive and therapeutic agents and it might contribute to p38 activation and JNKs phosphorylation during the SUV-induced DNA damage response (Oh, S. M., et al., Cancer Res, 2007. 67: p. 5186-94; and Liu, K., et al., Cancer Res, 2013. 73: p. 2181-8). Thus, identifying a novel compound that can prevent SUV-induced skin cancer by directly targeting TOPK is important compound 1 was synthesized as a potential TOPK inhibitor (FIG. 1A). To determine whether compound 1 exerted any cytotoxic effects against normal skin cells, JB6 P+ mouse epidermal skin cells and normal human dermal fibroblasts (NHDF) were treated with different concentrations of compound 1 for 24 or 48 h. The results showed that compound 1 had no cytotoxicity at concentrations less than 10 μM (FIGS. 6A and 6B). TOPK expression was examined in JB6, NHDF, A431 and SCC12 cells (FIG. 7). The results showed that TOPK is expressed at higher levels in skin carcinoma cells (A431 and SCC12) compared to normal skin cell lines (JB6 and NHDF). This suggests that compound 1 might specifically target skin carcinoma cells based on the higher expression of TOPK.

Figure 1B:
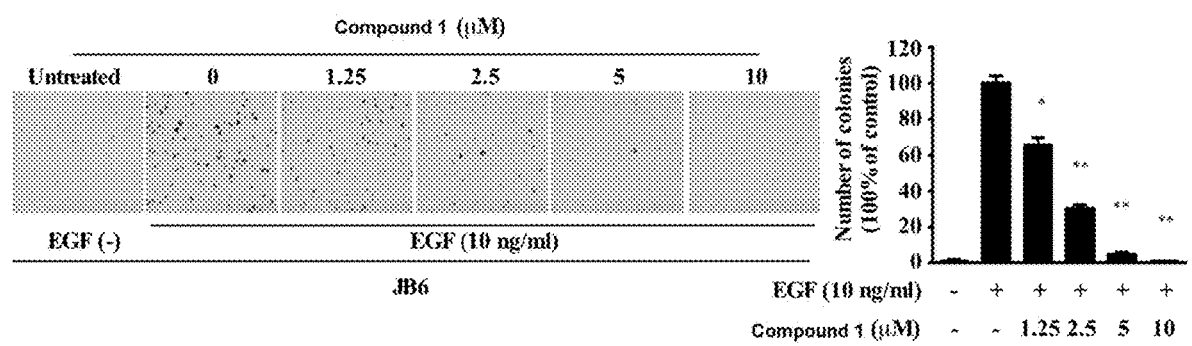
FIG. 1B shows compound 1 blocks EGF-induced neoplastic transformation of JB6 P+ cells. Cells were exposed to EGF (10 ng/ml) and treated with increasing concentrations of compound 1. Representative photographs are shown and data are presented as mean values±S.D. from triplicate experiments.
Figure 1C:
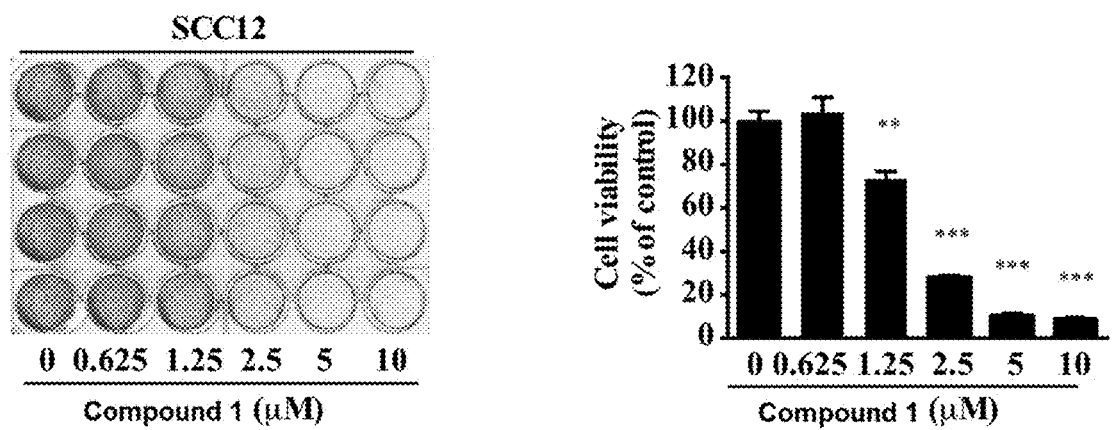
FIG. 1C shows compound 1 suppresses cell proliferation of SCC12 cell lines.
Figure 1D:
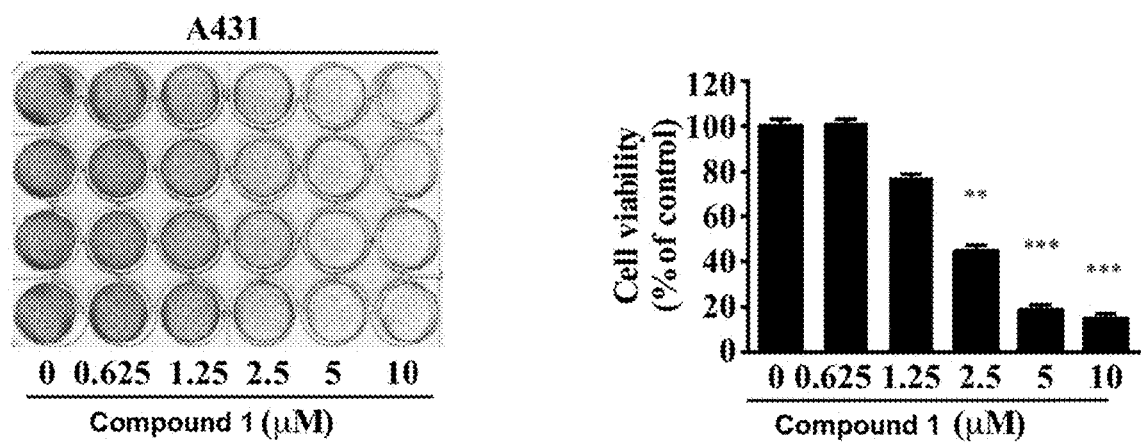
FIG. 1D shows compound 1 suppresses cell proliferation of or A431 cell lines. Cells were treated with different concentrations of compound 1 for several days and cell proliferation was determined by a crystal violet staining assay. The graph shows data from multiple experiments expressed as mean values±S.D. The asterisk (*) indicates a significant (*, p<0.05; , p<0.001; *, p<0.0001) decrease in cell proliferation with compound 1 treatment.
Figure 8:
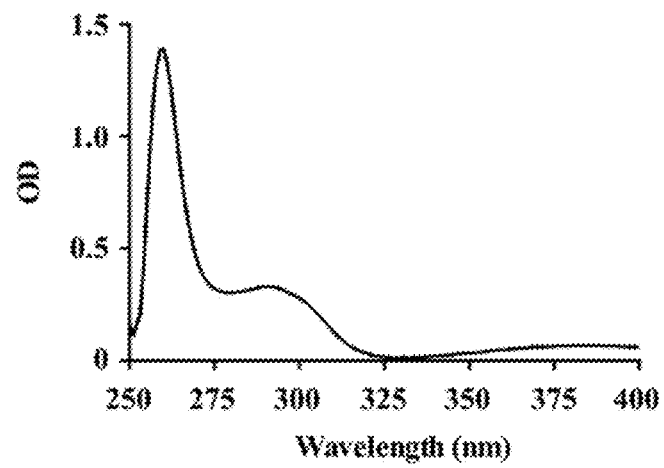
FIG. 8 shows measurement of compound 1 absorbance by spectrophotometer. Absorbance wavelengths of compound 1 were scanned using a Beckman DU®800 spectrophotometer.

In order to confirm whether compound 1 absorbs at UVA or UVB wavelengths, its ability to absorb SUV light between 250 and 320 nm was examined. The result indicated that compound 1 mainly absorbs light in the wavelength range of 250-275 nm and the peak absorption of compound 1 is 259 nm, which indicated that compound 1 did not show significant absorbance of UVA or UVB (FIG. 8). In addition, an anchorage-independent growth assay was performed to assess the effect of compound 1 on cell transformation. Data indicated that EGF-induced colony formation of JB6 P+ cells was attenuated after treatment with different concentrations of compound 1 (FIG. 1B). Similarly, cell proliferation was determined by a crystal violet staining assay. Results showed that compound 1 strongly decreased SCC12 and A431 cell proliferation in a dose-dependent manner (FIGS. 1C and 1D). Overall, these results indicated that compound 1 exhibited strong anti-tumor efficacy against NMSC cell growth and deserves further investigation.

Compound 1 Directly Suppresses TOPK Kinase Activity

Figure 2A:
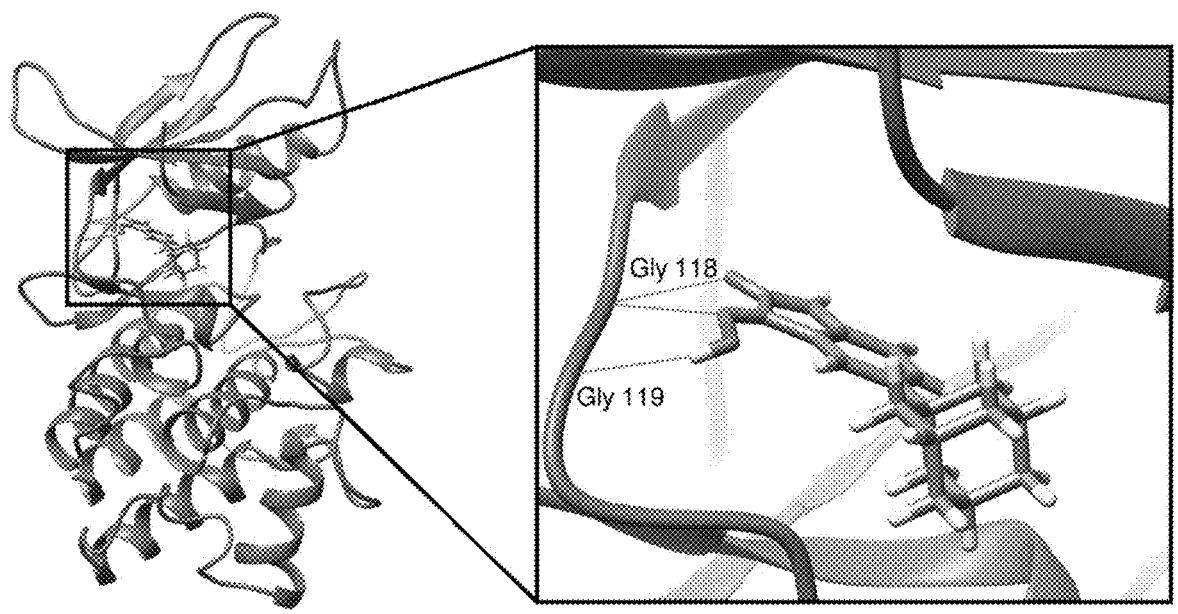
FIG. 2A shows computational docking model of compound 1 with TOPK.
Figure 2B:
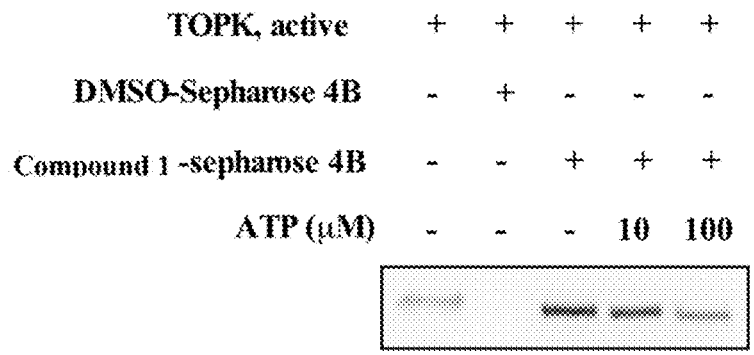
FIG. 2B shows compound 1 binds with TOPK in an ATP-competitive manner. Active TOPK (200 ng) was incubated with different concentrations of ATP (0, 10 or 100 μM) and then mixed with compound 1-conjugated Sepharose 4B beads or Sepharose 4B beads. Proteins were pulled down and analyzed by Western blot. Data are representative of 3 independent experiments that gave similar results.
Figure 2C:
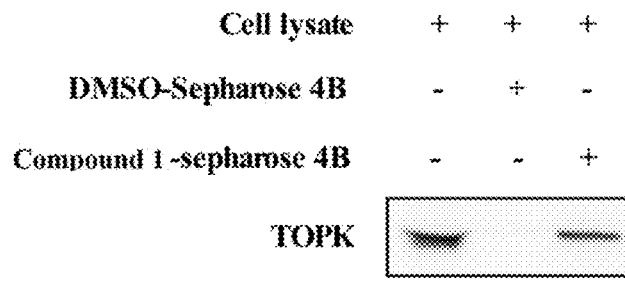
FIGS. 2C and 2D show compound 1 binds to either TOPK (2C) or MEK1/2 (2D) ex vivo. Lysates from HaCaT cells (500 μg) were incubated with compound 1-conjugated Sepharose 4B beads or Sepharose 4B beads alone and the pulled-down proteins were analyzed by Western blot. Data are representative of 3 independent experiments that gave similar results.
Figure 2D:
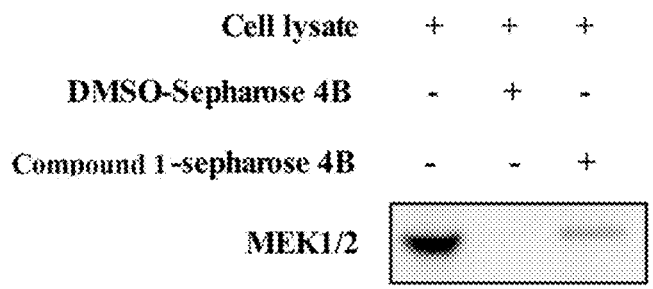
Figure 2E:
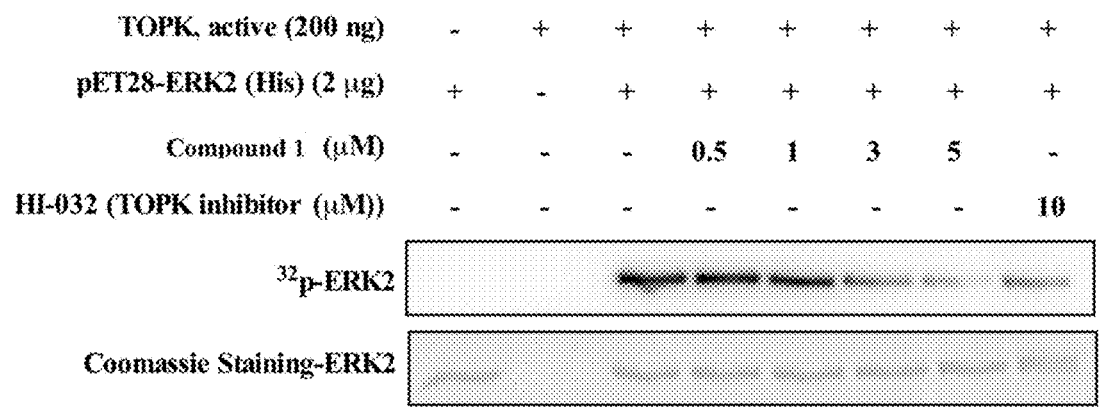
FIGS. 2E and 2F show compound 1 inhibits TOPK kinase (2E) activity but not MEK1 kinase (2F) activity in vitro. Active TOPK (200 ng) was mixed with compound 1 (0, 0.5, 1, 3, or 5 μM) or HI-032 (TOPK inhibitor, 10 μM) and then incubated with a [$\gamma$-$^{32}$P] ATP mixture. Similarly, MEK1 (200 ng) was mixed with compound 1 (0, 0.5, 1, 3, 5, or 10 μM) or PD098059 (MEK1 inhibitor, 5 μM) and then incubated with a [$\gamma$-$^{32}$P] ATP mixture. For 2E and 2F, the results are visualized by autoradiography and Coomassie blue staining serves as a loading control. Data are representative of 3 independent experiments that gave similar results.
Figure 2F:
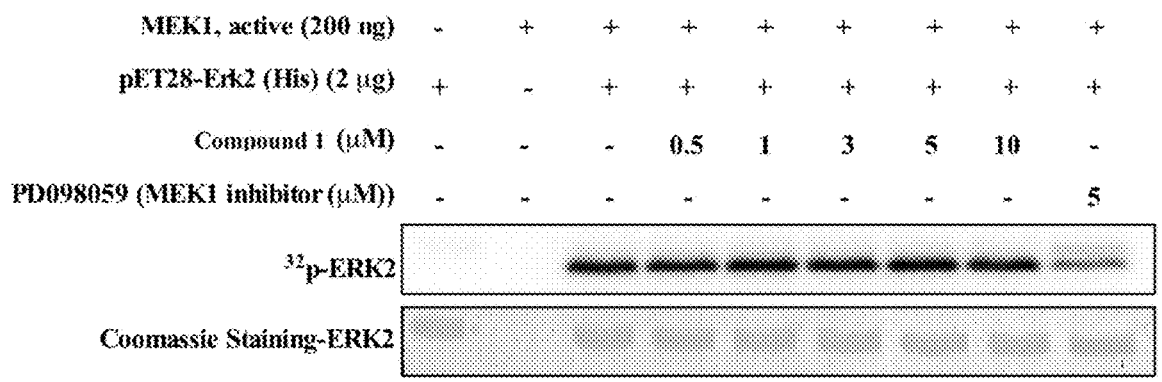
Figure 9:
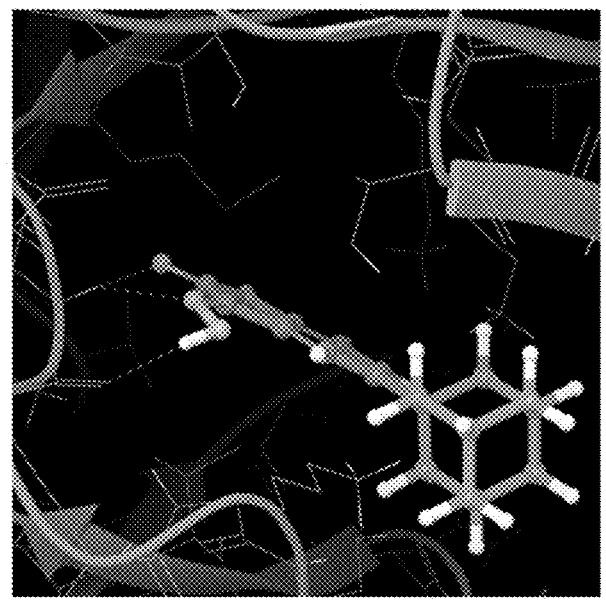
FIG. 9 shows the binding between compound 1 and TOPK is illustrated by Maestro in the Schrödinger Suite. The binding model shows that the hydrogen of glycine binds with oxygen and nitrogen of compound 1 to form hydrogen bonds. The oxygen atom of glycine binds with hydrogen of compound 1 to form a hydrogen bond.

To better understand the function of compound 1 in skin carcinogenesis, homology modeling and subsequent molecular docking were conducted to determine whether compound 1 binds to TOPK. The binding model indicated that compound 1 formed interactions within the ATP-binding pocket of TOPK and two potential hydrogen bonds were formed with the hinge residues Gly118 and Gly119 of TOPK and compound 1 (FIGS. 2A and 9). In addition, an ATP competition assay showed that the binding ability of compound 1 with TOPK was altered in the presence of ATP (FIG. 2B). Further, an in vitro binding assay was performed using compound 1-conjugated beads and HaCaT cell lysates. Results showed that both TOPK and MEK1/2 were detected in the compound 1-conjugated beads group but not in the beads only group (FIGS. 2C and 2D). Next, it is conducted an in vitro TOPK or MEK1 kinase activity assay with increasing concentrations of compound 1. The results indicated that compound 1 effectively inhibited TOPK kinase activity but not MEK1 activity (FIGS. 2E and 2F). Overall, the data suggested that compound 1 directly binds to TOPK and suppresses TOPK kinase activity.

Compound 1 Attenuates SUV-Induced TOPK Downstream Signaling

Figure 3A:
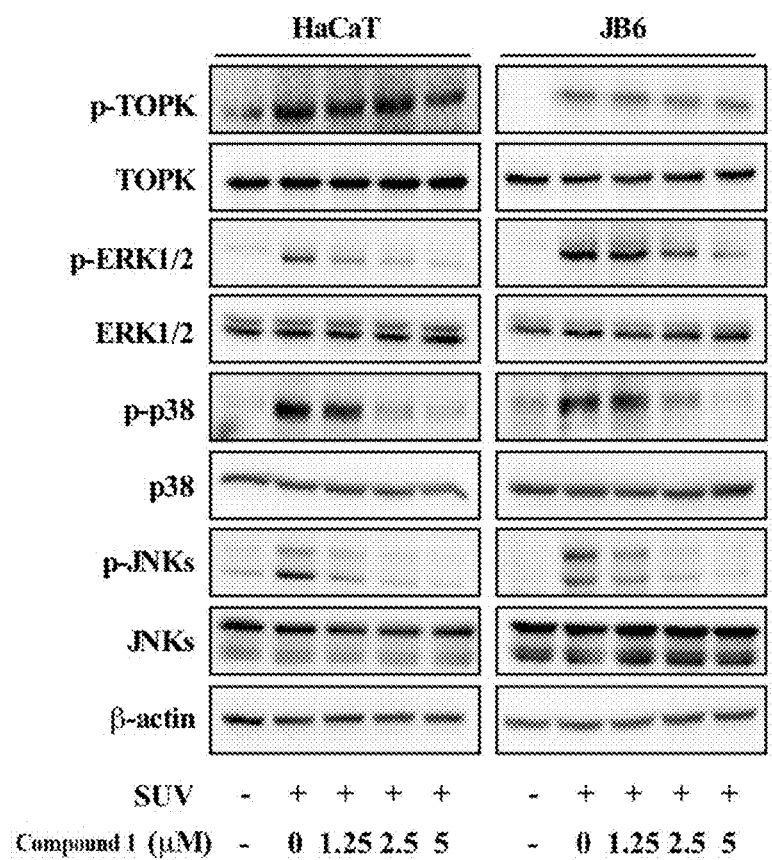
FIG. 3A shows compound 1 inhibits SUV-induced phosphorylation of ERK1/2, p38, and JNKs in HaCaT and JB6 P+ cell lines. The cells were cultured, treated for 4 h with different concentrations of compound 1 and then exposed to SUV (60 kJ UVA/m$^2$ and 2.9 kJ UVB/m$^2$), followed by an additional 15-minute incubation. Cells were harvested and the levels of phosphorylated and total proteins were determined by Western blot analysis with specific antibodies as indicated.
Figure 3B:
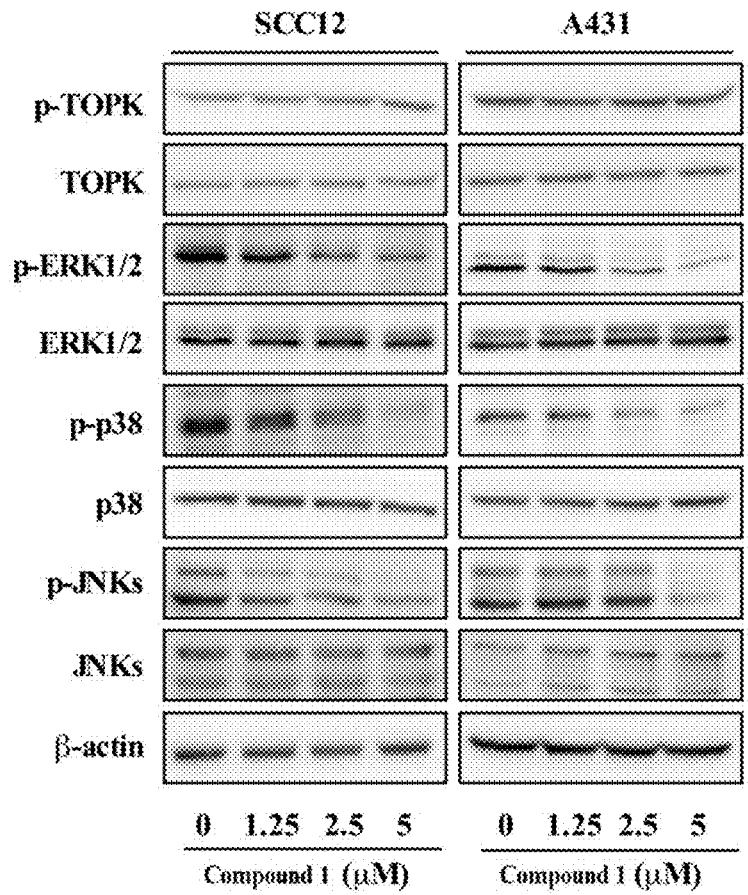
FIG. 3B shows compound 1 inhibits phosphorylation of ERK1/2, p38, and JNKs in SCC12 and A431 cell lines. The cells were cultured and treated with different concentrations of compound 1 for 24 h. Cells were harvested and the levels of phosphorylated and total proteins were determined by Western blot analysis with specific antibodies as indicated.
Figure 3C:
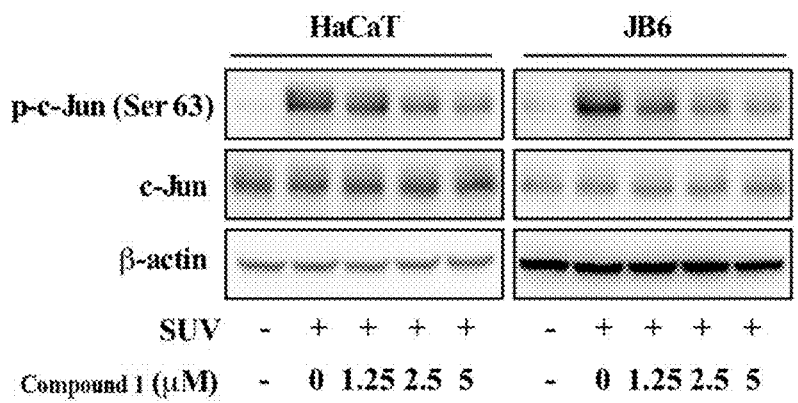
FIG. 3C shows compound 1 suppresses the phosphorylation c-Jun protein levels in HaCaT and JB6 P+ cells exposed to SUV (60 kJ UVA/m$^2$ and 2.9 kJ UVB/m$^2$).
Figure 3D:
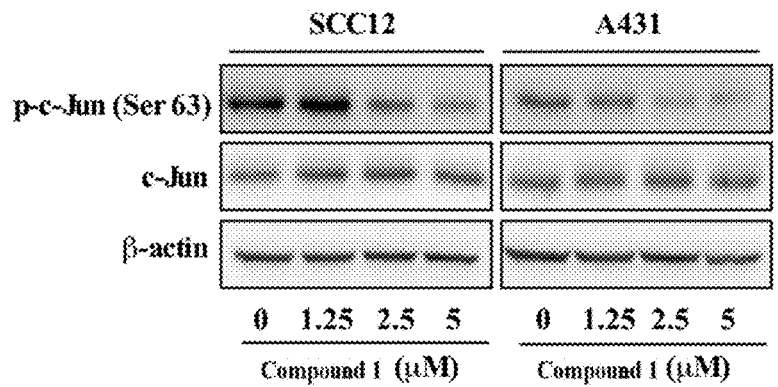
FIG. 3D shows compound 1 attenuates phosphorylation c-Jun protein levels in SCC12 and A431 cells dose-dependently.
Figure 3E:
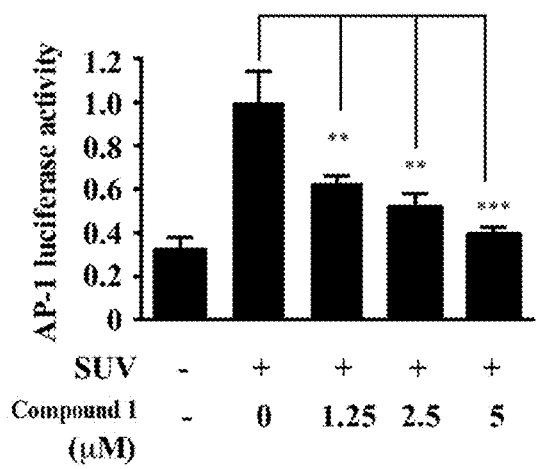
FIG. 3E shows compound 1 inhibits SUV-induced AP-1 activity. For the luciferase assay, JB6 P+ cells stably transfected with an AP-1 luciferase reporter plasmid were cultured. After starvation for 24 h, cells were treated for 1 h with compound 1 (0, 1.25, 2.5, or 5 μM). Cells were then exposed to SUV (60 kJ UVA/m$^2$ and 2.9 kJ UVB/m$^2$) and harvested 3 h later. Luciferase activity was measured and AP-1 activity is expressed relative to control cells without SUV treatment.
Figure 3F:
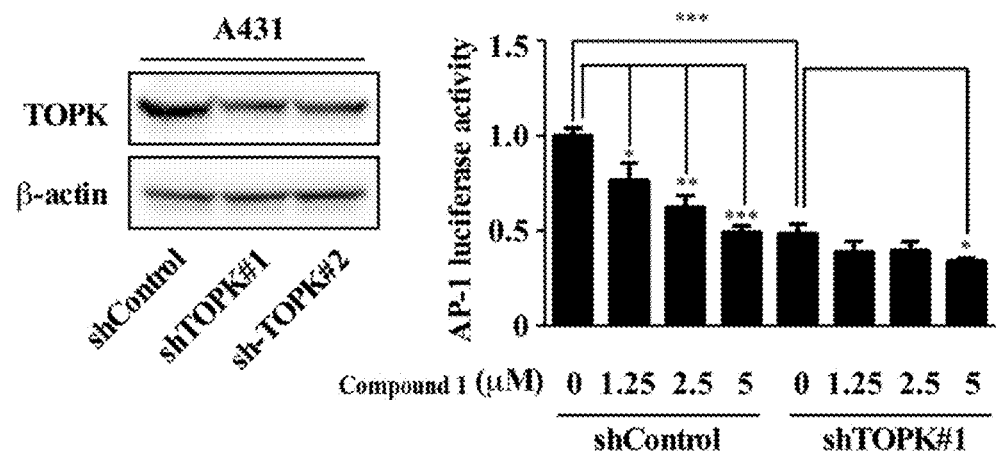
FIG. 3F shows compound 1 represses AP-1 activation in A431 cells and knockdown of TOPK also suppresses AP-1 activation. Knockdown of TOPK in A431 cell line (left). Stable control or TOPK knockdown cells were co-transfected with 100 ng of the AP-1 luciferase reporter plasmid and 50 ng of internal control P3-galactosidase plasmid. Cells were transfected using iMFectin poly DNA transfection reagent (GenDEPOT) according to the manufacturer's instructions. After 12 h of transfection, cells were incubated with the different concentrations of compound 1 for another 24 h. Luciferase and 3-galactosidase activities were measured using reagents included in the reporter assay system (right). Data are shown as mean values±S.D obtained from triplicate experiments. Significant differences were evaluated using one-way ANOVA and the asterisks (*) indicate a significant effect (*, $p<0.05$; , $p<0.001$; *, $p<0.0001$).

MAPK signaling cascades are well-known targets in SUV exposure and are involved in the regulation of SUV-induced cellular responses (Bode, A. M., et al., Sci STKE, 2003. 2003: p. Re2; Zykova, T. A., et al., J Biol Chem, 2010. 285: p. 29138-46; and Kim, Y., et al., Genes Dis, 2014. 1: p. 188-198). Particularly, the activation of the ERKs pathway is relevant to UVA, whereas activation of JNKs and p38 MAPKs is directly triggered by UVB or UVC irradiation (Kyriakis, J. M., et al., Physiol Rev, 2001. 81: p. 807-69; and Englaro, W., et al., Oncogene, 1998. 16: p. 661-4). Additionally, evidence indicated that hyperactivation of TOPK results in uncontrolled cell proliferation in many human cancers including skin cancer (Zhu, F., et al., Gastroenterology, 2007. 133: p. 219-31; Zykova, T. A., et al., J Biol Chem, 2010. 285: p. 29138-46; and Park, J. H., et al., Cancer Sci, 2010. 101: p. 403-11). Therefore, the effect of compound 1 on the SUV-induced TOPK signaling pathway in HaCaT and JB6 P+ cells was examined. At the same time the TOPK signaling pathway in SCC12 and A431 skin cancer cells was also examined after treatment with compound 1. Results showed that the level of phosphorylation of ERK1/2, p38, and JNKs in HaCaT and JB6 P+ cells exposed to SUV (60 kJ UVA/$m^2$ and 2.9 kJ UVB/$m^2$) was markedly suppressed after treatment with different concentrations of compound 1 (FIG. 3A). Similarly, the level of phosphorylation of ERK1/2, p38, and JNKs was blocked by compound 1 in SCC12 and A431 cells dose-dependently (FIG. 3B). Although no significant changes were observed in the phosphorylated and total TOPK protein levels, the results showed that compound 1 directly binds to TOPK and suppresses TOPK kinase activity, and then blocks the phosphorylation of ERK1/2, p38, and JNKs, which are the downstream of TOPK. Previous reports revealed that AP-1 could be activated by SUV irradiation through the MAPK cascades (Wang, J., et al., Cancer Res, 2005. 65: p. 6601-11; and Huang, C., et al., Oncogene, 1999. 18: p. 2828-35); and TOPK was involved in the UVB-induced JNK1-c-Jun-dependent signaling pathway leading to AP-1 activation (Oh, S. M., et al., Cancer Res, 2007. 67: p. 5186-94). Therefore, the protein levels of phosphorylation and total c-Jun by Western blot analysis were examined. The results indicated that the phosphorylated c-Jun protein levels in HaCaT and JB6 P+ cells exposed to SUV were significantly suppressed after treatment with different concentrations of compound 1 (FIG. 3C). Similarly, the protein levels of phosphorylated c-Jun were blocked dose-dependently by compound 1 in SCC12 and A431 cells (FIG. 3D). To examine the effect of compound 1 on SUV-induced transactivation of AP-1, JB6 P+ cells were stably exposed and transfected with an AP-1 luciferase reporter plasmid to compound 1 and SUV. The data showed that compound 1 inhibited SUV-induced transactivation of AP-1 (FIG. 3E) dose-dependently. Moreover, AP-1 activity was measured using a combination of compound 1 and knockdown of TOPK. The data indicated that AP-1 activity was suppressed after knockdown of TOPK in A431 cell line. More specifically, in the control group, the AP-1 activity was inhibited by compound 1 in a dose-dependent manner. However, in the TOPK knockdown group, the AP-1 activity was only slightly affected by compound 1 at the highest concentration (5 µM), which confirmed that compound 1 suppresses AP-1 activity by directly targeting TOPK (FIG. 3F). These results provide evidence showing that compound 1 treatment suppresses SUV-induced TOPK downstream signaling and AP-1 activity in NMSC cells. Based on these results, it is hypothesized that compound 1 might decrease SUV-induced carcinogenesis in vivo.

Compound 1 Suppresses SUV-Induced Skin Carcinogenesis in SKH-1 Hairless Mice

Figure 4A:
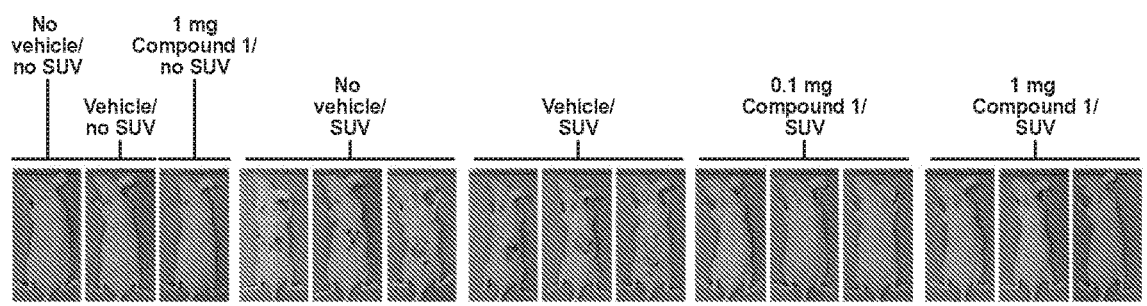
FIG. 4A shows external appearance of tumors.
Figure 4B:
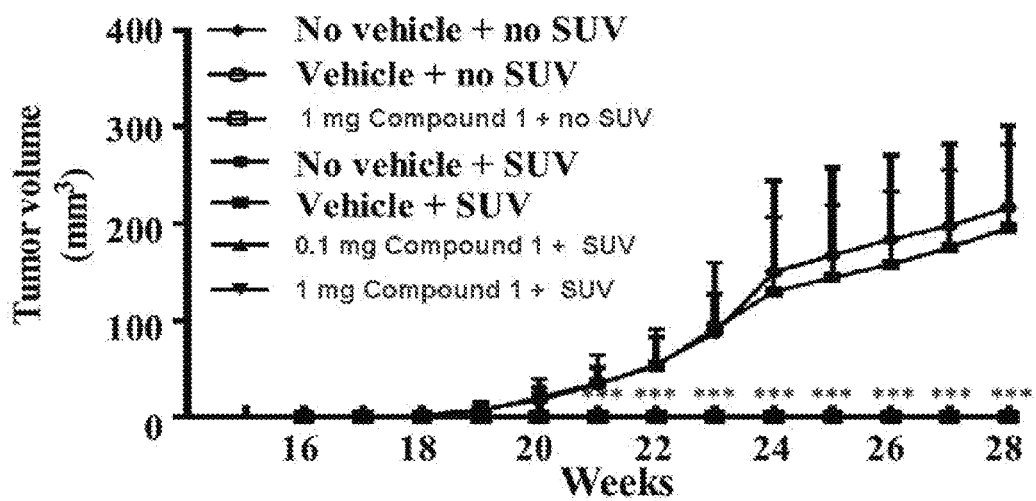
FIG. 4B shows compound 1 (Compound 1) suppresses SUV-induced tumor volume. Tumor volume was calculated according to the following formula: tumor volume (mm$^3$)=length×width× height×0.52.
Figure 4C:
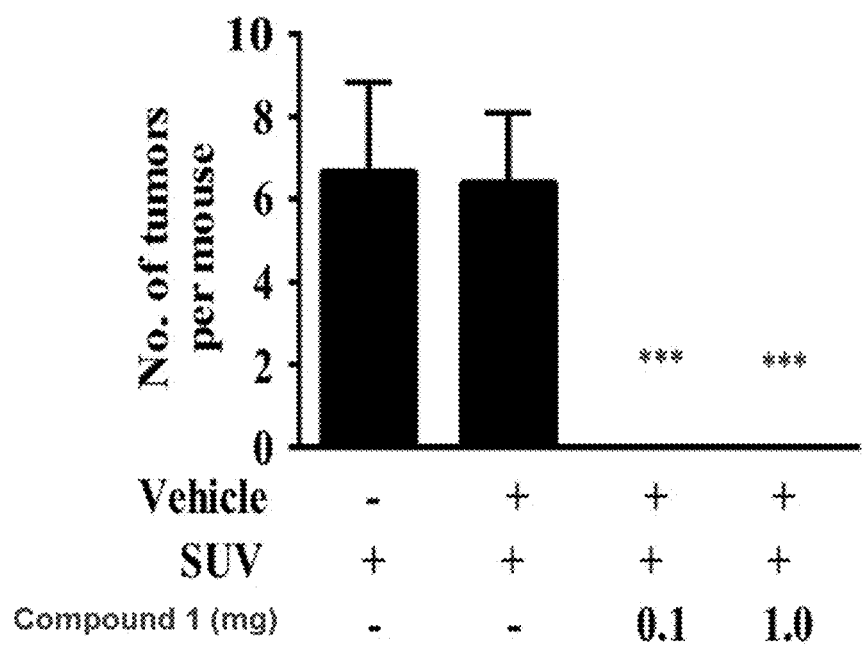
FIG. 4C shows compound 1 suppresses the average number of SUV-induced tumors at week 28. For 4B and 4C, data are represented as mean values±S.D. and significant differences were determined by one-way ANOVA. The asterisk (*) indicates a significant decrease compared to the SUV only or the vehicle and SUV-treated groups (*, $p<0.001$).
Figure 4D:
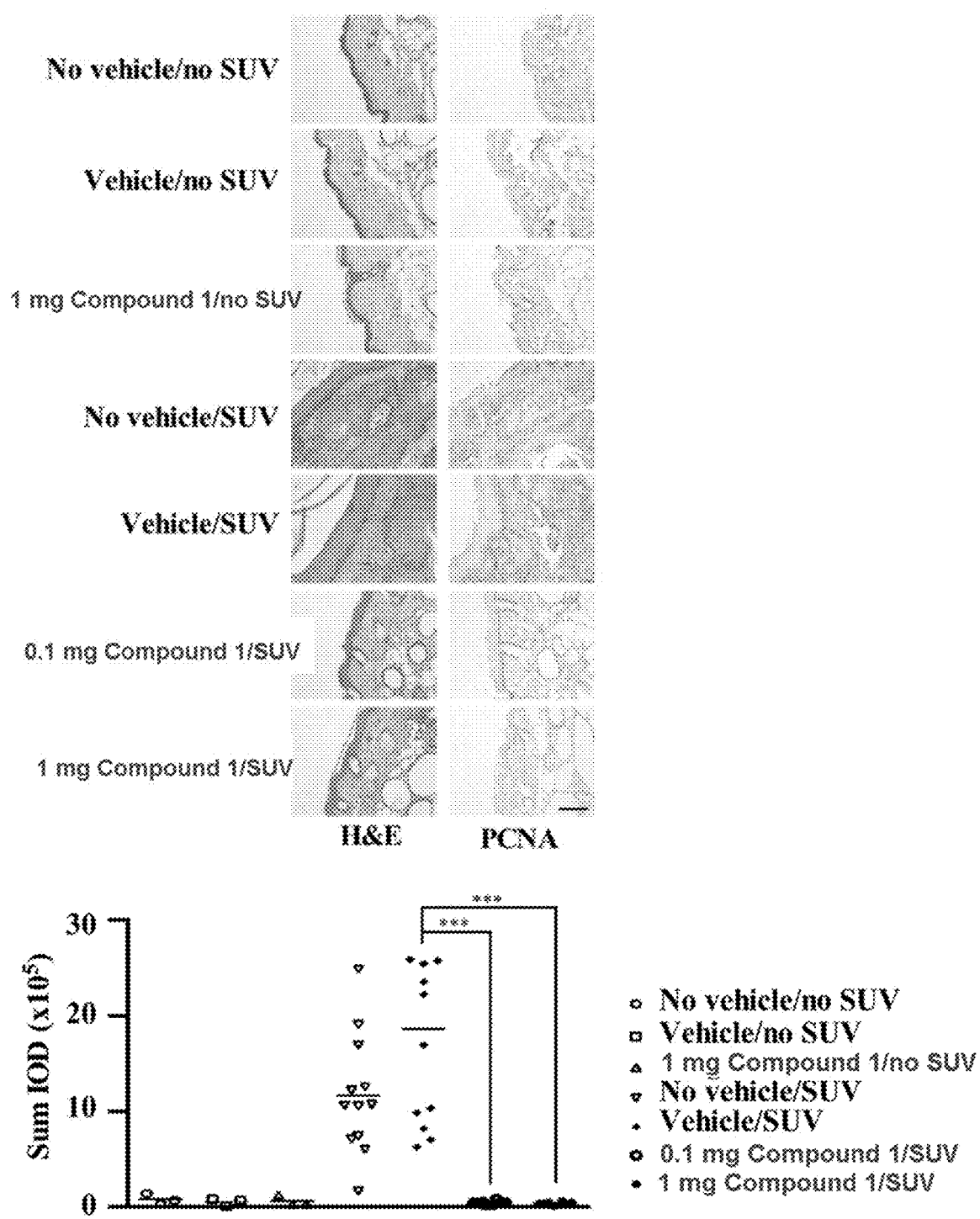
FIG. 4D shows compound 1 inhibits SUV-induced skin carcinogenesis in mouse skin epidermal tissue. Dorsal trunk skin samples were harvested and stained with H&E (left panels) or with an antibody to detect PCNA (right panels). Representative staining shows the pathologic changes in the epidermis from each of the groups (scale bar=100 μm). Expression of PCNA was quantified using Image-Pro Plus software and stained cells were counted from 5 separate areas on each slide (lower panel). An average of 3 samples was calculated per group. Data are expressed as mean percent of control±S.D. and the asterisks indicate a significant difference in PCNA expression (*, $p<0.001$).
Figure 4E:
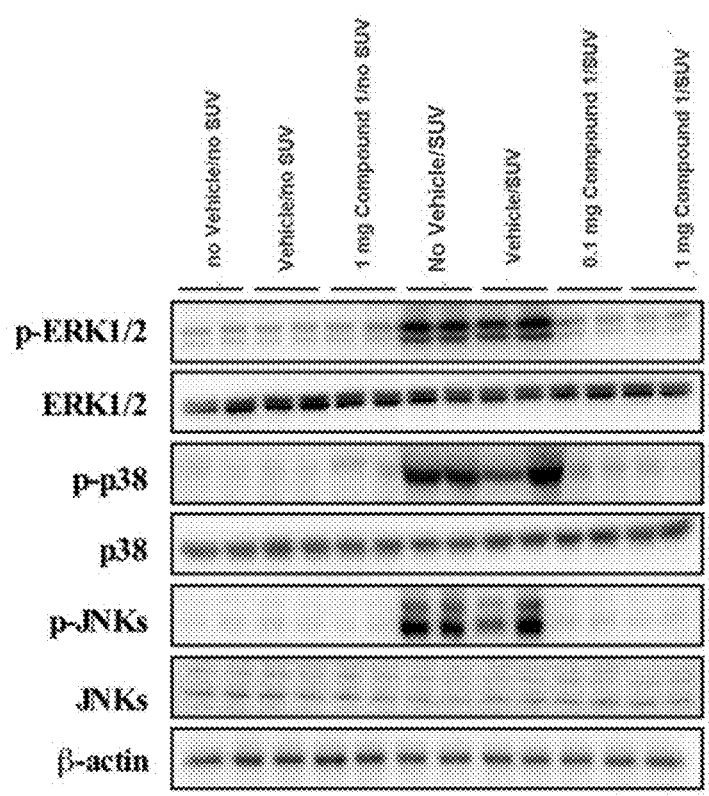
FIG. 4E shows compound 1 inhibits SUV-induced phosphorylation of ERK1/2, p38, and JNKs in mouse skin. The expression levels of phosphorylated and total proteins were analyzed by Western blot.
Figure 5A:
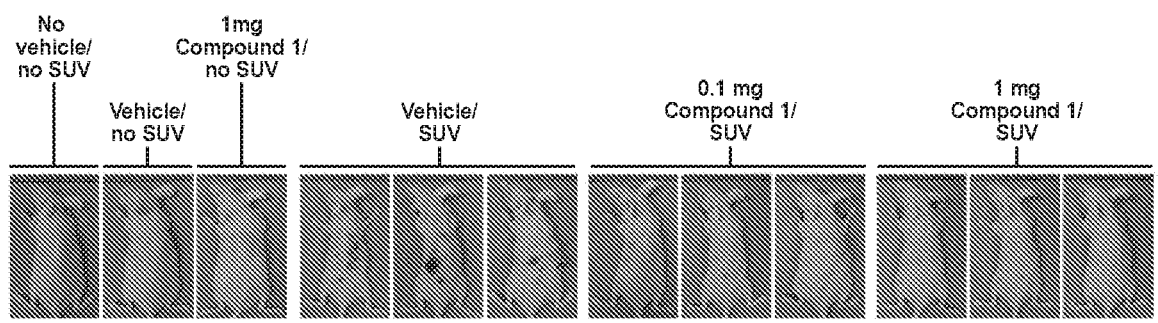
FIG. 5A shows external appearance of tumors.
Figure 5B:
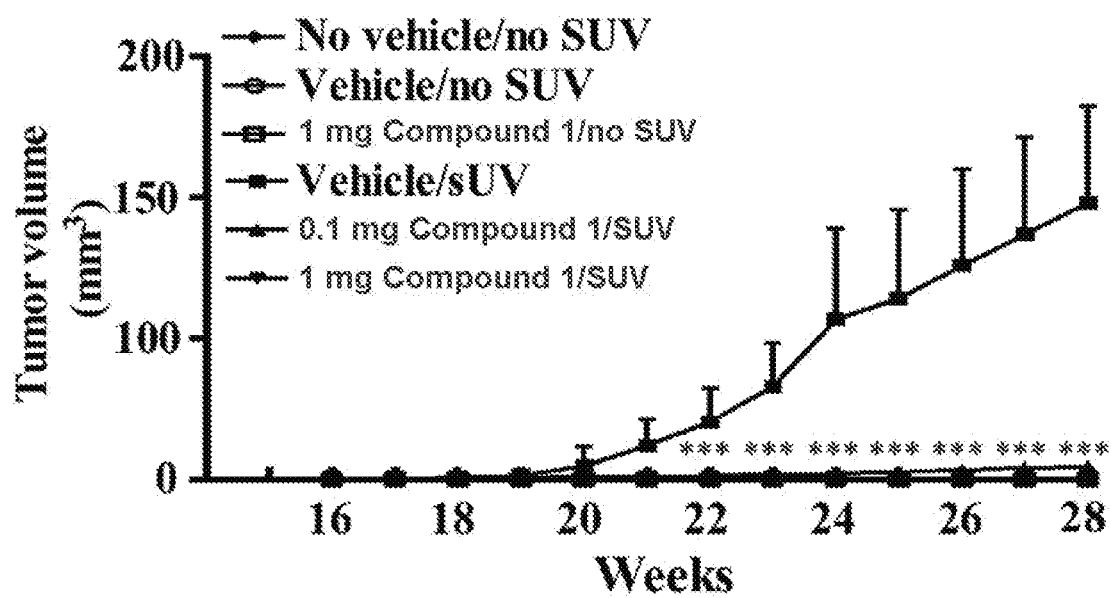
FIG. 5B shows compound 1 suppresses SUV-induced tumor volume. Tumor volume was calculated according to the following formula: tumor volume (mm$^3$)=length×width×height×0.52.
Figure 5C:
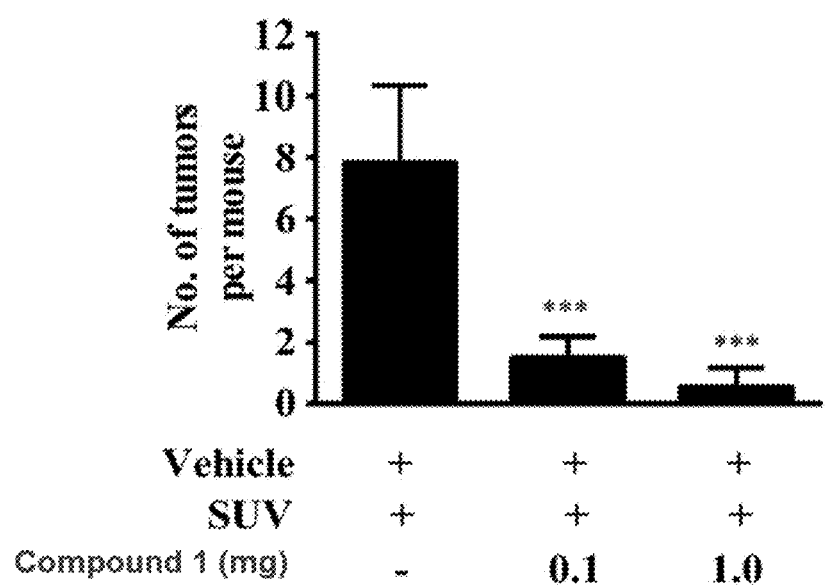
FIG. 5C shows compound 1 decreases the average number of SUV-induced tumors at week 28. For 5B and 5C, data are represented as mean values±S.D. and differences were determined by one-way ANOVA. The asterisk (*) indicates a significant decrease compared to the group exposed to SUV only or the group treated with vehicle followed by SUV (*, $p<0.001$).
Figure 5D:
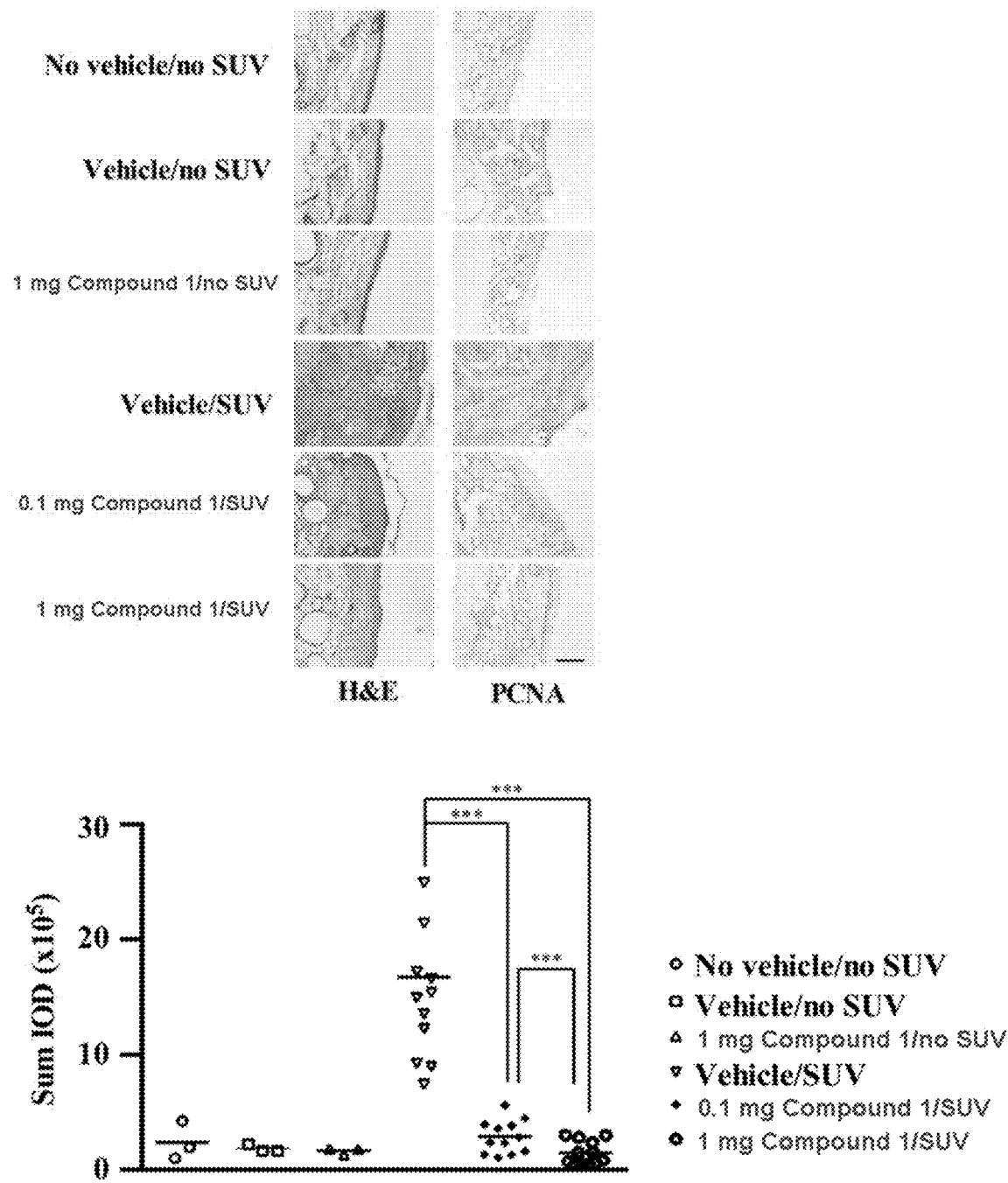
FIG. 5D shows compound 1 inhibits SUV-induced skin carcinogenesis in mouse skin epidermal tissue. Dorsal trunk skin samples were harvested and stained with H&E (left panels) or with an antibody to detect PCNA (right panels). Representative staining shows the pathologic changes in the epidermis from each of the groups (scale bar=100 μm). Expression of PCNA was quantified using Image-Pro Plus software and stained cells were counted from 5 separate areas on each slide (lower panel). An average of 3 samples was calculated per group. Data are expressed as mean percent of control±S.D. and the asterisks indicate a significant difference in PCNA expression (*, $p<0.001$).
Figure 10A:
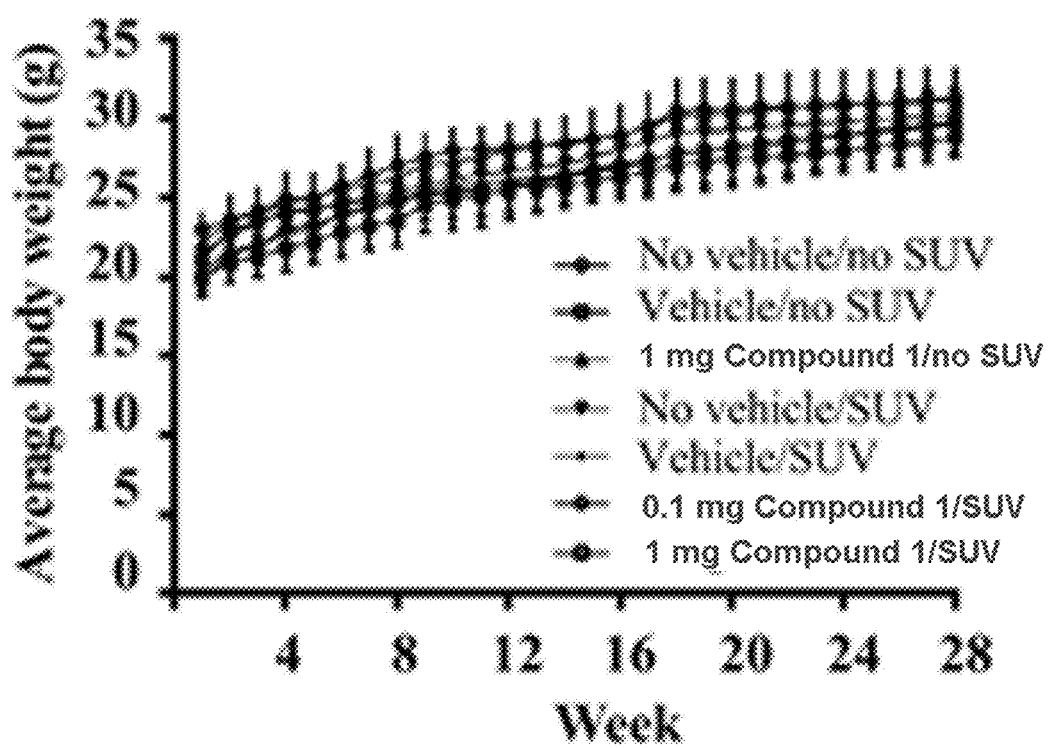
FIG. 10A shows average body weight of SKH-1 hairless mice. Mice were weighed once a week until the end of the study at week 28.
Figure 10B:
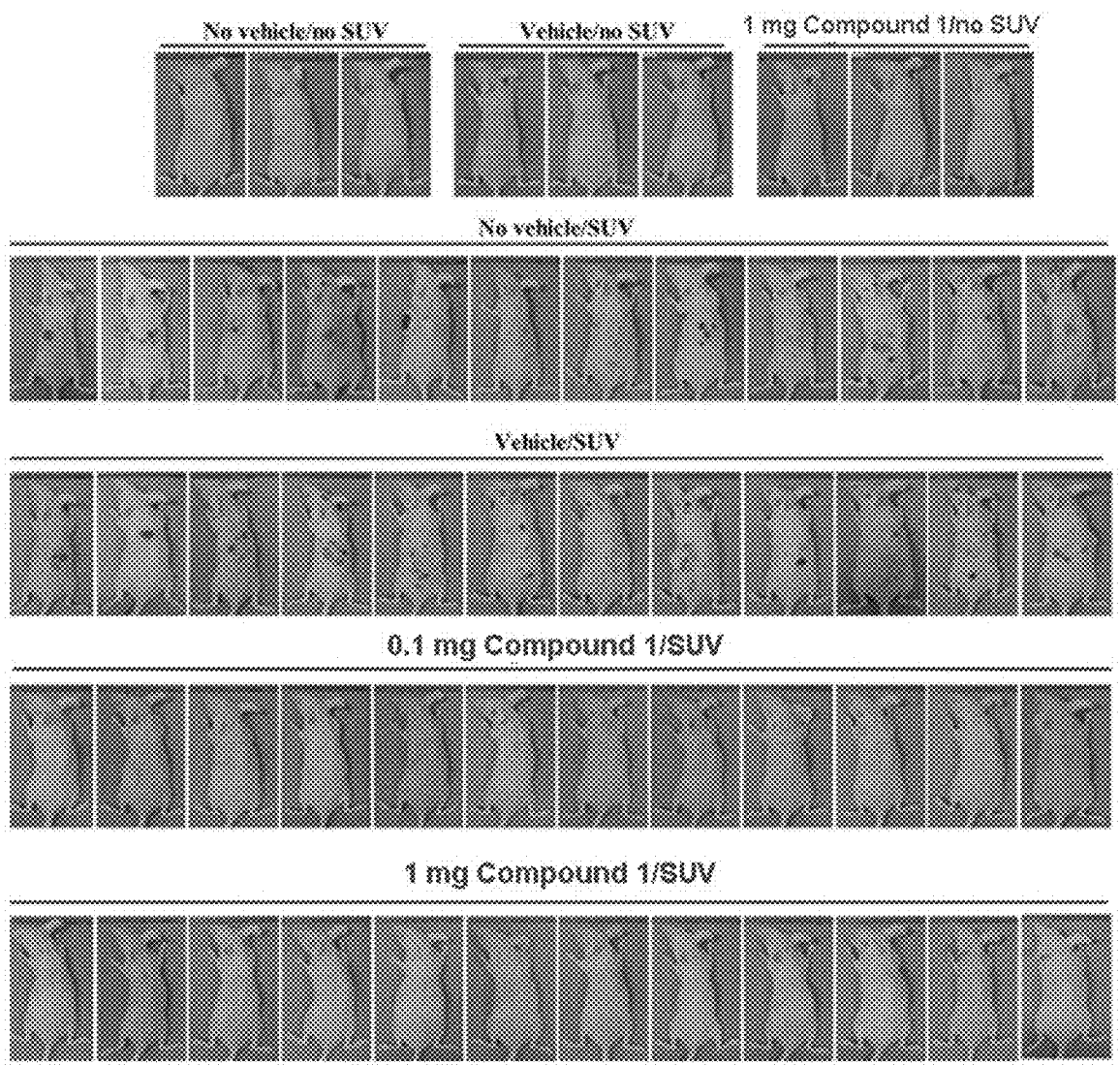
FIG. 10B shows external appearance of tumors. SKH-1 hairless mice were treated as described in Materials and Methods. The mice in the control groups (n=9) received no vehicle/no SUV (n=3), vehicle/no SUV (n=3), or 1 mg compound 17/no SUV (n=3), respectively. The mice in the SUV treated group received SUV only (n=12) and the mice in the vehicle/SUV-treated group (n=12) were treated with oil-in-water emulsion cream before SUV exposure. The mice in the 0.1 mg/SUV or 1 mg/SUV groups (n=12 each) received treatment with compound 1 (0.1 or 1 mg, respectively) before SUV exposure. The frequency of irradiation was set at 3 times a week for 15 weeks. The respective doses of oil-in-water emulsion cream or compound 1 were applied topically to the dorsal area. Tumor incidence and multiplicity were recorded weekly until the end of the experiment at week 28.
Figure 11A:
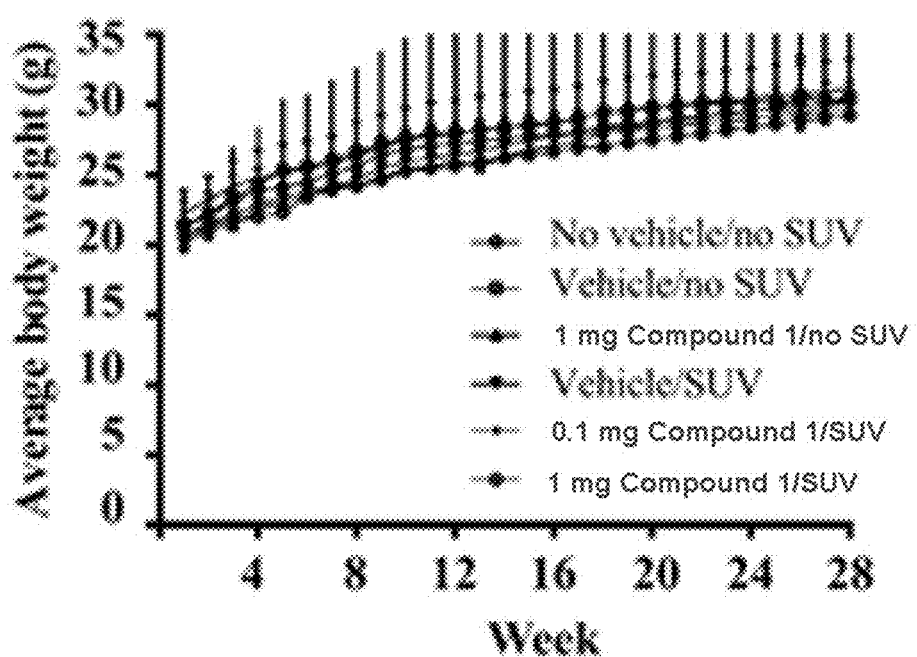
FIG. 11A shows average body weight of SKH-1 hairless mice. Mice were weighed once a week until week 28.
Figure 11B:
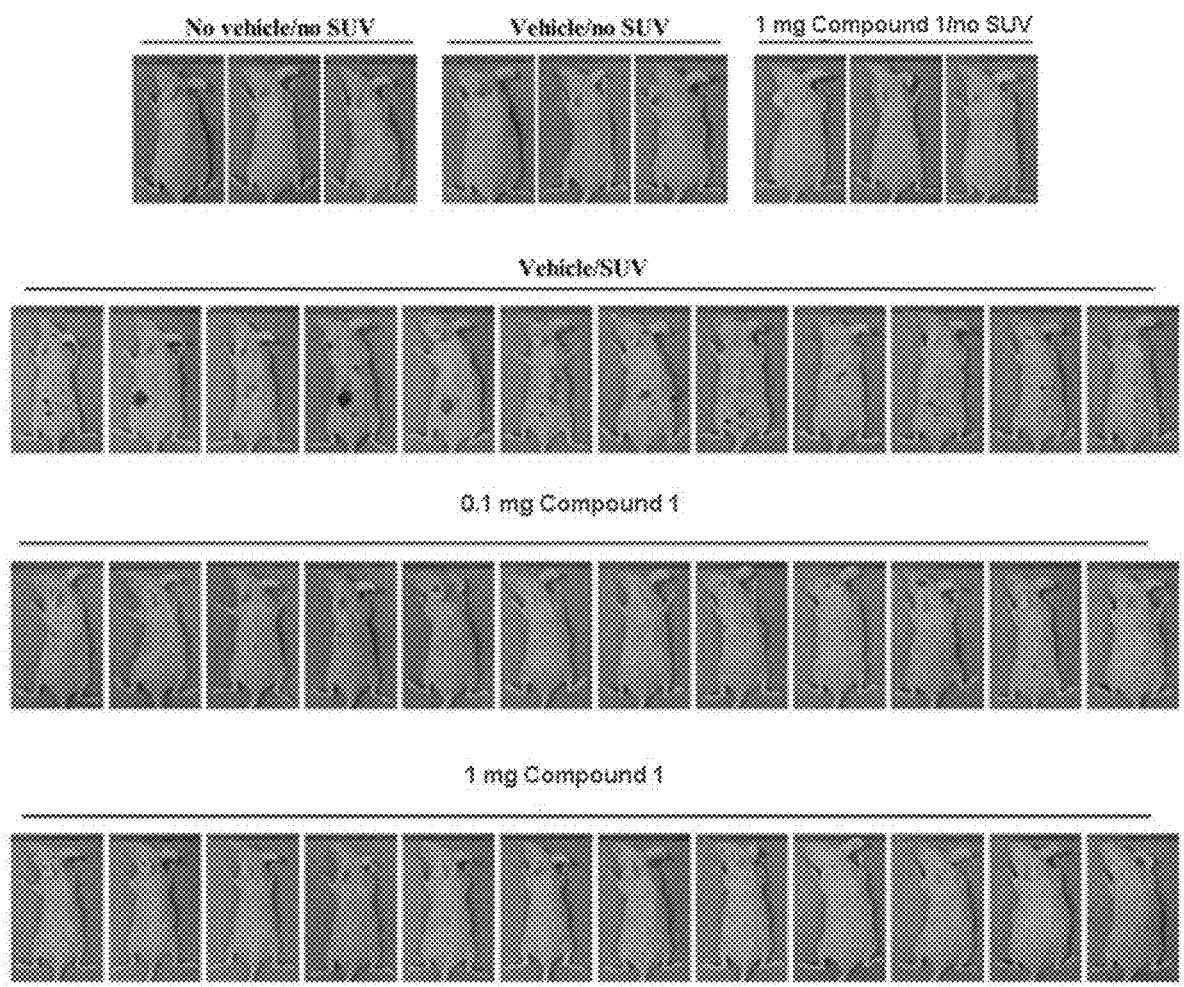
FIG. 11B shows external appearance of tumors. SKH-1 hairless mice were treated as described in Materials and Methods. The mice in the control groups (n=9) received no vehicle/no SUV (n=3), vehicle/no SUV (n=3), or 1 mg compound 1/no SUV (n=3), respectively. The mice in the rest of the groups received SUV irradiation for 15 weeks 3 times a week. The mice in the vehicle/SUV-treated group (n=12) were treated with oil-in-water emulsion cream 3 times a week until the end of the experiment (28 weeks). The mice in the 0.1 mg/SUV or 1 mg/SUV groups (n=12 each) received treatment with compound 1 (0.1 or 1 mg, respectively) 3 times a week until the end of the experiment (28 weeks). The respective doses of oil-in-water emulsion cream or compound 1 were applied topically to the dorsal area. Tumor incidence and multiplicity were recorded weekly until the end of the experiment at week 28.

SUV irradiation, comprising both UVA and UVB, more closely resembles the natural environment and exerts a variety of effects on cells and tissues. To study the chemopreventive effect and potential therapeutic value of compound 1 in vivo, two different SUV-induced mouse skin tumorigenesis models were used. Specifically, animal studies that included an early-stage prevention model (FIGS. 4, 10A and 10B) and a late-stage prevention model (FIGS. 5, 11A and 11B) were set up. Topical application of compound 1 on mouse dorsal skin had no effect on body weight (FIGS. 10A and 11A) but resulted in a total inhibition of SUV-induced papilloma formation in the early-stage prevention group (FIGS. 4A, 4B, 4C, and 10B), and a substantial suppression of SUV-induced tumor incidence in the late-stage prevention group (FIGS. 5A and 11B). Compared with the vehicle-treated group, although some papillomas were observed in the late-stage prevention study at 28 weeks after SUV exposure, results indicated that topical treatment with 0.1 or 1 mg compound 1 significantly reduced tumor volume and multiplicity (FIGS. 5B and C). Skin cancer development is well-known to be a multistep process, and SCCs frequently progress from actinic keratosis (AK), a sun-induced keratinocyte intraepithelial neoplasia (KIN or in situ cSCC) (Glogau, R. G., J Am Acad Dermatol, 2000. 42: p. 23-4). Thus, in order to evaluate the histopathological differences between each group, skin and tumor samples were processed for H&E staining at the end of the study (28 weeks). In the early-stage prevention study, results revealed that chronic SUV irradiation induced malignant SCCs in SUV-treated and vehicle and SUV-treated groups, respectively. However, treatment with 0.1 or 1 mg compound 1 decreased SUV-induced epidermal thickness, which represents typical changes in skin histological inflammation (FIG. 4D). Similarly, both AKs and SCCs were induced by SUV exposure in the late-stage prevention model. Notably, compound 1 dramatically decreased epidermal thickness and inhibited the formation of SCCs (FIG. 5D). Additionally, immunohistochemical data showed that PCNA, which is a well-known marker for evaluating cell proliferation, was significantly increased in the SUV- or vehicle and SUV-treated groups. In contrast, the expression of PCNA was decreased in the compound 1-treated groups, compared with the SUV- or vehicle and SUV-treated groups in both prevention models (FIGS. 4D and 5D). Moreover, Western blot analysis of mouse skin showed that phosphorylation of ERK1/2, p38, and JNKs induced by SUV was dramatically suppressed in the compound 1-treated groups (FIGS. 4E and 5E). Overall, these results clearly indicated that compound 1 exerts a strong preventive effect and also has potential therapeutic value against SUV-induced mouse skin carcinogenesis through its inhibition of TOPK activation.

DISCUSSION

Solar ultraviolet (SUV) irradiation represents the most important environmental risk factor that is involved in the development of skin cancer (Bowden, G. T., Nat Rev Cancer, 2004. 4: p. 23-35; and Leiter, U., et al., Adv Exp Med Biol, 2008. 624: p. 89-103). Studies demonstrated that accumulated SUV irradiation exposure leads to an increased risk of both BCC and SCC and nearly 90% of NMSC is estimated to be caused by chronic exposure to SUV (Seebode, C., et al., Anticancer Res, 2016. 36: p. 1371-8; Pleasance, E. D., et al., Nature, 2010. 463: p. 191-6), Particularly, an early sign of SUV-induced skin cancer is the development of AKs, which have been identified as precursors to SCC. Epiderniological evidence demonstrated that approximately 0.025-16% of AKs progress into invasive SCCs within one year, whereas approximately 26% of AKs spontaneously regress within one year (Glogau, R. G., J Am Acad Dermatol, 2000. 42: p. 23-4; and Marks, R., Lancet, 1988. 1: p. 795-7). Thus, SCC is preventable and oft-en curable if detected early. An accumulation of evidence indicated that specific proteins are involved in SUV-induced skin carcinogenesis. Specifically, approximately 88% of human skin cancers contain p53 mutations (Kanjilal, S., et al., Cancer Res, 1995. 55: p. 3604-9) and activating RAS mutations have been found in UV-induced mouse skin cancers (Pierceall, W. E., et al. Cancer Res, 1992. 52: p. 3946-51), The importance of EGER, RSK2, ERKs and COX-2 in U V-induced skin carcinogenesis has also been reported in the past few years (Oi, N., et al., Cancer Prev Res (Phila), 2012. 5: p. 1103-14; Yao, K., et al., Cancer Prev Res (Phila), 2014. 7: p. 958-67; Yang, G., et al., Cancer Prev Res (Phila), 2014. 7: p. 1056-66; and Fischer, S. M., et al., Mol Carcinog, 1999. 25: p. 231-40). Interestingly, TOPK, a newly identified oncogene, has been studied in a wide range of human cancers (Zhu, F., et al., Gastroenterology, 2007. 133: p. 219-31; and Hu, F., et al., Oncogene, 2010. 29: p. 5464-74). Although previous studies indicated that TOPK is highly expressed in melanoma and clinical samples of solar dermatitis (Zykova, T. A., et al., J Biol Chem, 2010. 285: p. 29138-46; and Fan, X., et al., Oncotarget, 2016. 7: p. 24633-45), only one potential TOPK inhibitor against SUV-induced skin inflammation has been discovered. In the current study, a novel TOPK inhibitor referred to as compound 1 was identified (FIG. 1A) and showed its potential chemopreventive or therapeutic effects against SUV-induced skin carcinogenesis.

As indicated earlier, MAPK signaling pathways are activated during UV-induced carcinogenesis. Disturbance of the MAPK cascades by UV occurs rapidly and can lead to cellular malfunction, altered gene expression or loss of cell cycle control, which further contributes to the formation of cancer cells (de Gruijl, F. R., et al., J Photochem Photobiol B, 2001. 63: p. 19-27). The p38 and JNKs proteins, which are subgroups of the MAPK family, are highly expressed in solar dermatitis (Fan, X., et al., Oncotarget, 2016. 7: p. 24633-45), and both play significant roles in SUV-induced inflammation and apoptosis (Chouinard, N., et al., Biochem J, 2002. 365: p. 133-45; Hildesheim, J., et al., J Invest Dermatol, 2004. 122: p. 497-502; Chen, Y. R., et al., J Biol Chem, 1996. 271: p. 31929-36; Hochedlinger, K., et al., Oncogene, 2002. 21: p. 2441-5; and Tournier, C., et al., Science, 2000. 288: p. 870-4). ERK1/2 are well-characterized MAP kinases. They are activated in keratinocytes following SUV irradiation and are involved in regulating cell proliferation, differentiation, apoptosis and tumnorigenesis (He, Y. Y., et al., J Biol Chem, 2004. 279: p. 53867-74; Kim, H. H., et al., J Lipid Res, 2005. 46: p. 1712-20; and Muthusamy, V., et al., Arch Dermatol Res, 2010. 302: p. 5-17). TOPK is an upstream kinase of p38 and JNKs and can phosphorylate ERK1/2 (Zhu, F., et al., Gastroenterology, 2007. 133: p. 219-31). Abnormal levels of TOPK can signal downstream, triggering the activation of the ERK1/2, p38 or JNKs pathways. In the present study, it is demonstrated that ERKs signaling, as well as p38 MAPKs and JNKs signaling, was strongly enhanced by SU V irradiation (FIG. 3A). However, our findings indicated that compound 1 not only dramatically suppressed SUV-induced activation of ERK1/2, p38 or JNKs in HaCaT and JB6 P+ cells, but also decreased MAPK signaling in skin cancer cells (FIGS. 3A and 3B). Evidently, the activator protein-1 (AP-1) transcription factor is crucial for skin cancer development (Eckert, R. L., et al., J Skin Cancer, 2013. 2013: p. 537028) and the activity of AP-1 is increased by SUV exposure through the activation of the MAPK signaling pathways (Bode, A. M., et al., Sci STKE, 2003. 2003: p. Re2). Moreover, TOPK was involved in the UVB-induced JNK1-c-Jun-dependent signaling pathway leading to AP-J. activation (Oh, S. M., et al., Cancer Res, 2007. 67: p. 5186-94). The data clearly showed that SUV-induced transactivation of AP-1 was inhibited by compound 1 dose-dependenly (FIG. 3E). Similarly, the AP-1 activity was significantly suppressed by compound 1 in a dose-dependent manner in A431 cells, whereas after knock-down of TOPK only showed a slight decrease of AP-1 activity at the highest concentration of compound 1 (FIG. 3F). More directly, results of an in vitro kinase assay showed that compound 1 effectively inhibited TOPK kinase activity, but not MEK1 activity (FIGS. 2E and 2F). Collectively, our findings further suggested that the chemopreventive or therapeutic effects of compound 1 against SUV-induced skin carcinogenesis might be due to the specific inhibition of TOPK.

Evidence indicated that only 3 TOPK inhibitors, H I-TOPK-032, OTS514 and Cefradine have been discovered (Kim, D. J., et al., Cancer Res, 2012. 72: p. 3060-8; Matsuo, Y., et al., Sci Transl Med, 2014. 6: p. 259ra145; and Fan, X., et al., Oncotarget, 2016. 7: p. 24633-45). However, the chemopreventive or therapeutic effects of these compounds against SUV-induced skin carcinogenesis have not yet been studied. Importantly, our in vivo results showed that compound 1 was an effective chemopreventive agent and a potential therapeutic agent against SUV-induced skin tumorigenesis. The SKH-1 hairless mouse is widely considered to be the most suitable model for studies of SUV-induced carcinogenesis, and also is very useful for the study of topical compounds that alter SUV-induced skin cancer development (Oi, N., et al., Cancer Prev Res (Phila), 2012. 5: p. 1103-14; Benavides, F., et al., J Dermatol Sci, 2009. 53: p. 10-8; and Lee, D. E., et al., J Biol Chem, 2011. 286: p. 14246-56). Generally, skin tumors are induced in mice by chronic exposure to SUV, and tumors progress from foci of epithelial hyperplasia to premalignant papillomas and ultimately into a malignant SCC (Benavides, F., et al., J Dermatol Sci, 2009. 53: p. 10-8). In this study, the system of SUV irradiation mimics natural sunlight that includes both UVA and UVB spectrums. Results indicated that SCCs were successfully induced by 15 weeks of SUV exposure (3 times a week) in the SKH-1 hairless mouse models. Importantly, the topical application of compound 1 completely suppressed the incidence of SUV-induced skin cancer development in an early-stage prevention study (FIGS. 4A-4E and 10A-10B). In addition, it was shown that SKH-1 mice exposed to SUV and treated with topical compound 1 displayed a significantly decreased tumor incidence, multiplicity, volume and malignancy rate compared to vehicle-treated mice in the late-stage prevention study (FIGS. 5A-5E and 11A-11B). These data support the idea that cumulative length of SU V exposure is a risk factor for SUV-induced NMSC and highlights the fact that compound 1 might ultimately decrease skin carcinogenesis through its direct inhibition of TOPK Example 3

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents (including Gao, G., et al., Mol Cancer Ther, 2017, 16(9), 1843-1854) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

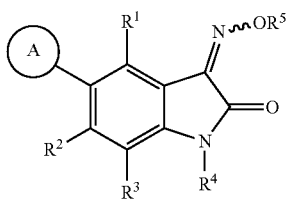

I wherein:
ring A is a 3-15 membered cycloalkyl that is optionally substituted with one or more groups selected from halo, hydroxy, nitro, cyano, $NR^aR^b$, $C_{1-6}$ alkyl, $C_{1-6}$ alkoxy, or $C_{1-6}$ haloalkyl,
$R^1$ is hydrogen, halo, hydroxy, nitro, cyano, $NR^cR^d$, $C_{1-6}$ alkyl, $C_{1-6}$ alkoxy, or $C_{1-6}$ haloalkyl;
$R^2$ is hydrogen, halo, hydroxy, nitro, cyano, $NR^eR^f$, $C_{1-6}$ alkyl, $C_{1-6}$ alkoxy, or $C_{1-6}$ haloalkyl;
$R^3$ is hydrogen, halo, hydroxy, nitro, cyano, $NR^gR^h$, $C_{1-6}$ alkyl, $C_{1-6}$ alkoxy, or $C_{1-6}$ haloalkyl;
$R^4$ is hydrogen, $C_{1-6}$ alkyl, or $C_{1-6}$ haloalkyl;
$R^5$ is hydrogen, $C_{1-6}$ alkyl, aryl, or heteroaryl, wherein the $C_{1-6}$ alkyl is optionally substituted with one or more groups selected from halo, aryl, heteroaryl, hydroxy, $C_{1-6}$ alkoxy, carboxy, or $NR^iR^j$;
each of $R^a$ and $R^b$ is independently selected from H and $C_{1-6}$ alkyl, or $R^a$ and $R^b$ together with the nitrogen to which they are attached form aziridino, azetidino, morpholino, piperazino, pyrrolidino or piperidino;
each of $R^c$ and $R^d$ is independently selected from H and $C_{1-6}$ alkyl, or $R^c$ and $R^d$ together with the nitrogen to which they are attached form aziridino, azetidino, morpholino, piperazino, pyrrolidino or piperidino;
each of $R^e$ and $R^f$ is independently selected from H and $C_{1-6}$ alkyl, or $R^e$ and $R^f$ together with the nitrogen to which they are attached form aziridino, azetidino, morpholino, piperazino, pyrrolidino or piperidino; and
each of $R^g$ and $R^h$ is independently selected from H and $C_{1-6}$ alkyl, or $R^g$ and $R^h$ together with the nitrogen to which they are attached form aziridino, azetidino, morpholino, piperazino, pyrrolidino or piperidino; and
each of $R^i$ and $R^j$ is independently selected from H and $C_{1-6}$ alkyl, or $R^i$ and $R^j$ together with the nitrogen to which they are attached form aziridino, azetidino, morpholino, piperazino, pyrrolidino or piperidino;
or a salt thereof.

2. The compound of claim 1, wherein A is a 6-12 membered cycloalkyl that is optionally substituted with one or more groups selected from halo, hydroxy, nitro, cyano, $NR^aR^b$, $C_{1-6}$ alkyl, $C_{1-6}$ alkoxy, or $C_{1-6}$ haloalkyl.

3. The compound of claim 1, wherein A is a 8-11 membered cycloalkyl that is optionally substituted with one or more groups selected from halo, hydroxy, nitro, cyano, $NR^aR^b$, $C_{1-6}$ alkyl, $C_{1-6}$ alkoxy, or $C_{1-6}$ haloalkyl.

4. The compound of claim 1, wherein A is adamantyl.
5. The compound of claim 1, wherein $R^1$ is hydrogen.
6. The compound of claim 1, wherein $R^2$ is hydrogen.
7. The compound of claim 1, wherein $R^3$ is hydrogen.
8. The compound of claim 1, wherein $R^4$ is hydrogen.
9. The compound of claim 1, which is:

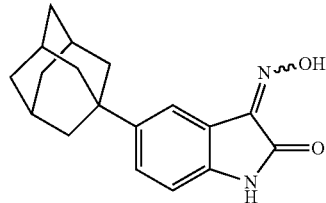 [SMILES: O=C1Nc2ccc(C34CC5CC(CC(C5)C3)C4)cc2C1=NO]

or a salt thereof.

10. A pharmaceutical composition comprising a compound of formula I as described in claim 1, or a pharmaceutically acceptable salt thereof, and a pharmaceutically acceptable carrier.

11. A method to treat cancer associated with activity of TOPK in an animal having said cancer comprising administering a compound of formula I as described in claim 1, or a pharmaceutically acceptable salt thereof, to the animal.

12. The method of claim 11, wherein the cancer is selected from the group consisting of skin cancer, pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors.

13. The method of claim 11, wherein the cancer is skin cancer.

14. The method of claim 11, wherein the cancer is solar ultraviolet (SUV)-induced skin cancer.

15. A method to inhibit the activity of T-LAK cell-originated protein kinase (TOPK) in vitro or in vivo comprising contacting the kinase with a compound of formula I as described in claim 1, or a pharmaceutically acceptable salt thereof.

* * * * *